United States Patent
Albaugh et al.

(12) 
(10) Patent No.: US 6,399,604 B1
(45) Date of Patent: *Jun. 4, 2002

(54) SUBSTITUTED 4-OXO-NAPTHYRIDINE-3-CARBOXAMIDES; GABA BRAIN RECEPTOR LIGANDS

(75) Inventors: Pamela A. Albaugh, Clinton; Robert W. DeSimone, Durham, both of CT (US); Gang Liu, Agoura, CA (US)

(73) Assignee: Neurogen Corporation, Branford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/634,093

(22) Filed: Aug. 8, 2000

Related U.S. Application Data

(63) Continuation of application No. 09/139,456, filed on Aug. 25, 1998, now Pat. No. 6,143,760.
(60) Provisional application No. 60/056,799, filed on Aug. 25, 1997.

(51) Int. Cl.[7] .................. A61K 31/535; A61K 31/44; C07D 413/00; C07D 471/02
(52) U.S. Cl. .................. 514/235.2; 514/300; 544/128; 546/123
(58) Field of Search .............. 514/300, 235.2; 546/123; 544/128

(56) References Cited

U.S. PATENT DOCUMENTS

| | | | |
|---|---|---|---|
| 3,953,428 A | | 4/1976 | Murakami et al. |
| 4,374,138 A | | 2/1983 | Haskell et al. |
| 4,621,088 A | | 11/1986 | Laruelle et al. |
| 5,378,679 A | | 1/1995 | Neubling et al. |
| 6,143,760 A | * | 11/2000 | Albaugh et al. |

FOREIGN PATENT DOCUMENTS

| | | |
|---|---|---|
| DE | 2322750 | 11/1973 |
| DE | 2407744 | 8/1974 |
| DE | 279875 A1 | 6/1990 |
| DE | 279887 A1 | 6/1990 |
| DE | 295 360 A5 | 10/1991 |
| PL | 125299 | 2/1982 |

OTHER PUBLICATIONS

G. White et al., (1995). Harwood Academic Publishers GmbH., Receptors and Channels, "*Human α and β Subunits Contribute to the EC50 GABA at the GABAa Receptor Expressed in Xenopus Oocytes*". vol. 3, pp. 1–5.

Geoffrey White and David Gorley, (1995). Molecular Neuroscience, NeuroReport., "*Benzodiazepine site inverse agonists can selectively inhibit subtypes of the GABA a receptor.*" vol. 6, pp. 1313–1316.

Kondo Kazumi, Patent Abstracts of Japan, vol. 13. No. 260. Jun. 15, 1999.

J. Heindl et al., *Eur. J. Med. Chem.*, vol. 6, ppl 549–555, 1977.

* cited by examiner

*Primary Examiner*—D. Margaret Seaman
(74) *Attorney, Agent, or Firm*—McDonnell Boehnen Hulbert & Berghoff

(57) ABSTRACT

The present invention encompasses structures of the Formula

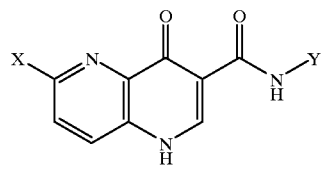

or the pharmaceutically acceptable non-toxic salts thereof wherein:

X is hydrogen, halogen, (un)substituted alkyl, (un)substituted alkoxy or amino; and Y is (un)substituted alkyl, aryl, or heteroaryl, which compounds are highly selective agonists, antagonists or inverse agonists for GABAa brain receptors or prodrugs of agonists, antagonists or inverse agonists for GABAa brain receptors. These compounds are useful in the diagnosis and treatment of anxiety, Down Syndrome, sleep, cognitive and seizure disorders, and overdose with benzodiazepine drugs and for enhancement of alertness.

107 Claims, No Drawings

SUBSTITUTED 4-OXO-NAPTHYRIDINE-3-CARBOXAMIDES; GABA BRAIN RECEPTOR LIGANDS

This application is a continuation of U.S. patent application Ser. No. 09/139,456, filed Aug. 25, 1998, now U.S. Pat. No. 6,143,760, which claims priority from U.S. Provisional Appl. No. 60/056,799, filed Aug. 25, 1997.

BACKGROUND OF THE INVENTION

1. Field of the Invention

This invention relates to substituted 4-oxg-napthyridine-3-carboxamides and, in particular, such compounds which selectively bind to GABAa receptors. This invention also relates to pharmaceutical compositions comprising such compounds and to the use of such compounds in enhancing alertness and treating anxiety, overdoses of benzodiazepine-type drugs, Down Syndrome, and sleep, seizure and cognitive disorders.

2. Description of the Related Art

γ-Aminobutyric acid (GABA) is regarded as one of the major inhibitory amino acid transmitters in the mammalian brain. Over 40 years have elapsed since its presence in the brain was demonstrated (Roberts & Frankel, J. Biol. Chem 187: 55–63, 1950; Udenfriend, J. Biol. Chem. 187: 65–69, 1950). Since that time, an enormous amount of effort has been devoted to implicating GABA in the etiology of seizure disorders, sleep, anxiety and cognition (Tallman and Gallager, Ann. Rev. Neuroscience 8: 21–44, 1985). Widely, although unequally, distributed through the mammalian brain, GABA is said to be a transmitter at approximately 30% of the synapses in the brain. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Drugs that interact at the GABAa receptor can possess a spectrum of pharmacological activities depending on their abilities to modify the actions of GABA.

The 1,4-Benzodiazepines, such as diazepam, continue to be among the most widely used drugs in the world as anxiolytics, sedative-hypnotics, muscle relaxants, and anti-convulsants. A number of these compounds are extremely potent drugs; such potency indicates a site of action with a high affinity and specificity for individual receptors. Early electro-physiological studies indicated that a major action of benzodiazepines was enhancement of GABAergic inhibition. Presently, those compounds possessing activity similar to the benzodiazepines are called agonists. Compounds possessing activity opposite to benzodiazepines are called inverse agonists, and the compounds blocking both types of activity have been termed antagonists.

The GABAa receptor subunits have been cloned from bovine and human cDNA libraries (Schoenfield et al., 1988; Duman et al., 1989). A number of distinct cDNAs were identified as subunits of the GABAa receptor complex by cloning and expression. These are categorized into α, β, γ, δ, ε, and provide a molecular basis for the GABAa receptor heterogeneity and distinctive regional pharmacology (Shivvers et al., 1980; Levitan et al., 1989). The γ subunit appears to enable drugs like benzodiazepines to modify the GABA responses (Pritchett et al., 1989). The presence of low Hill coefficients in the binding of ligands to the GABAa receptor indicates unique profiles of subtype specific pharmacological action.

With the discovery of the "receptor" for the benzodiazepines and the subsequent definition of the nature of the interaction between GABA and the benzodiazepines, it appears that the behaviorally important interactions of the benzodiazepines with different neurotransmitter systems are due in a large part to the enhanced ability of GABA itself to modify these systems. Each modified system, in turn, may be associated with the expression of a behavior. Depending on the mode of interaction, these compounds are capable of producing a spectrum of activities (either sedative, anxiolytic, and anticonvulsant, or wakefulness, seizures, and anxiety).

Various 1,4-dihydro-4-oxo-1,5-naphthyridine-3-carboxylic acids and esters have been disclosed. See, for example, Eur. J. Med. Chem.-Chim. Ther. (1977), 12 (6), 549–55.

Polish Patent No. 125299 discloses compounds of the formula:

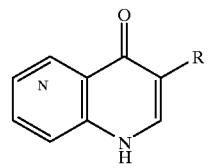

wherein N denotes a ring nitrogen in the 5- or 6-position, and R is $CO_2H$ or $CO_2Et$.

Several 1,4-dihydro-4-oxo-1,5-napthyridine-3-carboxamide derivatives of penicillin said to possess antibacterial activity have been disclosed. For example, German Patent. No. DD 279887 discloses a compound of the formula

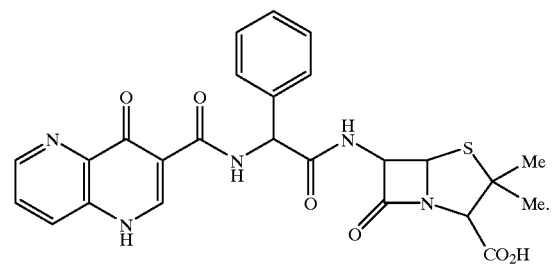

Japanese Patent No. 72-45118 discloses ampicillin derivatives of 1,4-dihydro-4-oxo-3-naphthyridines.

SUMMARY OF THE INVENTION

This invention provides novel compounds of Formula I which interact with a GABAa binding site, the benzodiazepine receptor.

The invention provides pharmaceutical compositions comprising compounds of Formula I. The invention also provides compounds useful in the diagnosis and treatment of anxiety, Down Syndrome, sleep, cognitive and seizure disorders, and overdose with benzodiazepine drugs and for enhancement of alertness. Accordingly, a broad embodiment of the invention is directed to compounds of Formula I:

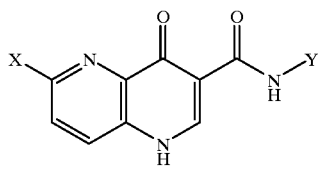

wherein:
- X is hydrogen, halogen, —OR$_1$, C$_1$–C$_6$ alkyl optionally substituted with up to three groups selected independently from halogen and hydroxy, or —NR$_2$R$_3$;
- X is phenyl, naphthyl, 1-(5,6,7,8-tetrahydro)naphthyl or 4-(1,2-dihydro)indenyl, pyridinyl, pyrimidyl, isoquinolinyl, 1,2,3,4-tetrahydroisoquinolinyl, benzofuranyl, benzothienyl, each of which is optionally substituted with up to three groups selected from halogen, C$_1$–C$_5$ alkyl, C$_1$–C$_4$ alkoxy, C$_1$–C$_5$ alkylthio, hydroxy, amino, mono or di(C$_1$–C$_6$)alkylamino, cyano, nitro, trifluoromethyl or trifluoromethoxy; or
- X represents a carbocyclic group ("the X carbocyclic group") containing from 3–7 members, up to two of which members are optionally hetero atoms selected from oxygen and nitrogen, where the X carbocyclic group is optionally substituted with one or more groups elected from halogen, alkoxy, mono- or dialkylamino, sulfonamide, azacycloalkyl, cycloalkylthio, alkylthio, phenylthio, or a heterocyclic group;
- Y is lower alkyl having 1–8 carbon atoms optionally substituted with up to two groups selected from halogen, alkoxy, mono- or dialkylamino, sulfonamide, azacycloalkyl, cycloalkylthio, alkylthio, phenylthio, a heterocyclic group, —OR$_4$, —NR$_5$R$_6$, SR$_7$, or aryl; or
- Y is a carbocyclic group ("the Y carbocyclic group") having from 3–7 members atoms, where up to three of which members are optionally hetero atoms selected from oxygen and nitrogen and where any member of the Y carbocyclic group is optionally substituted with halogen, —OR$_4$, —NR$_5$R$_6$, SR$_7$, aryl or a heterocyclic group;
- R$_1$ is hydrogen, lower alkyl having 1–6 carbon atoms, or cycloalkyl having 3–7 carbon atoms, where each alkyl may be optionally substituted with —OR$_4$, or —NR$_5$R$_6$;
- R$_2$ and R$_3$ are the same or different and represent
  - hydrogen, lower alkyl optionally mono- or disubstituted with alkoxy, aryl, halogen, or mono- or di-lower alkyl;
  - aryl or aryl(C$_1$–C$_6$)alkyl where each aryl is optionally substituted with up to three groups selected from halogen, hydroxy, C$_1$–C$_6$ alkyl, C$_1$–C$_6$ alkoxy, or mono- or di(C$_1$–C$_6$)alkylamino;
  - cycloalkyl having 3–7 carbon atoms optionally mono or disubstituted with halogen, alkoxy, or mono- or di-lower alkyl; or
  - —SO$_2$R$_8$;
- R$_4$ is as defined for R$_1$;
- R$_5$ and R$_6$ carry the same definitions as R$_2$ and R$_3$, respectively;
- R$_7$ is hydrogen, lower alkyl having 1–6 carbon atoms, or cycloalkyl having 3–7 carbon atoms; and
- R$_8$ is lower alkyl having 1–6 carbon atoms, cycloalkyl having 3–7 carbon atoms, or optionally substituted phenyl.

These compounds are highly selective agonists, antagonists or inverse agonists for GABAa brain receptors or prodrugs of agonists, antagonists or inverse agonists for GABAa brain receptors. These compounds are useful in the diagnosis and treatment of anxiety, Down Syndrome, sleep, cognitive and seizure disorders, and overdose with benzodiazepine drugs and for enhancement of alertness.

DETAILED DESCRIPTION OF THE INVENTION

The novel compounds encompassed by the invention can be described by the general Formula I set forth above.

In Formula I above, —NR$_2$R$_3$ can also represent a heterocyclic group such as, for example, piperidine in the case where R$_2$ and R$_3$ together form a C$_5$-alkylene group. Further, R$_2$ and R$_3$ together may represent an alkylene or alkenylene group optionally containing up to two heteroatoms selected from nitrogen and oxygen. The resulting groups include imidazolyl, pyrrolidinyl, morpholinyl, piperazinyl, and piperidinyl.

Similarly, the —NR$_5$R$_6$ group in Formula I above can also represent a heterocyclic group such as, for example, piperidine in the case where R$_5$ and R$_6$ together form a C$_5$-alkylene group. Further, R$_5$ and R$_6$ together may represent an alkylene or alkenylene group optionally containing up to two heteroatoms selected from nitrogen and oxygen. The resulting groups include imidazolyl, pyrrolidinyl, morpholinyl, piperazinyl, and piperidinyl.

Preferred compounds of Formula I are those where X represents (C$_1$–C$_6$)alkoxy, more preferably (C$_1$–C$_3$)alkoxy. Particularly preferred compounds of Formula I include methoxy or ethoxy as the X group.

Still other preferred compounds of Formula I include those where the Y is lower alkyl, e.g., methyl or ethyl, substituted with phenyl, pyridyl, or pyrimidinyl. A more preferred Y group is benzyl optionally substituted with halogen, (C$_1$–C$_6$)alkyl, (C$_1$–C$_6$)alkoxy, amino, or mono- or di(C$_1$–C$_6$)alkyl.

Where R$_2$ and R$_3$ in Formula I represent optionally substituted aryl or aryl(C$_1$–C$_6$)alkyl, the aryl group is preferably phenyl, pyridyl, or pyrimidinyl and the alkyl groups are preferably methyl and ethyl. More preferred are benzyl and phenyl. Particularly preferred is benzyl.

Where X is optionally substituted C$_1$–C$_6$ alkyl, the alkyl group is preferably optionally substituted methyl, ethyl, or propyl. More preferred are perhalomethyl and trihaloethyl. Preferred halogens are fluorine. Particularly preferred is 2,2,2-trifluoroethyl.

X in Formula I may be an optionally substituted phenyl, naphthyl, 1-(5,6,7,8-tetrahydro)naphthyl, 4-(1,2-dihydro)indenyl, pyridinyl, pyrimidyl, isoquinolinyl, benzofuranyl, or benzothienyl group, or preferably a 1,2,3,4-tetrahydroisoquinolinyl group.

In addition to the compounds of Formula I, the invention encompasses compounds of Formula IA

IA

[Structure of formula IA: a 1,5-naphthyridinone with X substituent and C(O)NH-Y carboxamide]

wherein:

X is
(i) hydrogen, halogen, mono- or dialkylamino, alkoxy,
(ii) a group of the formula:

[R$_1$O-G-O- group]

where G is lower alkylene having 1–6 carbon atoms, or a cyclic group of the formula

[cyclic group with (CH$_2$)$_n$ and (CH$_2$)$_m$]

where n is 0, 1, or 2, and m is an integer of from 1 to 5, with the proviso that the sum of n+m is not less than 1 or greater than 5; and R$_1$ is hydrogen, lower alkyl, or (C$_3$–C$_7$)cycloalkyl, where the alkyl or cycloalkyl is optionally substituted with halogen, lower alkoxy, or mono- or di(C$_1$–C$_6$)alkylamino;

(iii) a group of the formula:

[R$_3$R$_2$N-G-O- group]

where
G is as defined above for ii; and
R$_2$ and R$_3$ independently represent hydrogen, lower alkyl having 1–6 carbon atoms, cycloalkyl having 3–7 carbon atoms, —SO$_2$R$_8$ where R$_8$ is (C$_1$–C$_6$) alkyl, (C$_3$–C$_7$)cycloalkyl, or optionally substituted phenyl, or
R$_2$ and R$_3$ together with the nitrogen atom to which they are attached form a heterocyclic moiety such as imidazolyl, pyrrolidinyl, morpholinyl, piperazinyl, or piperidinyl;

(iv) a group of the formula:

[R$_4$O-G-N(R$_2$)- group]

where
R$_2$ is as defined above for iii;
R$_4$ is hydrogen, lower alkyl having 1–6 carbon atoms, or cycloalkyl having 3–7 carbon atoms, and may be optionally substituted with one or more (C$_1$–C$_6$)alkoxy or mono- or di(C$_1$–C$_6$) alkylamino groups; and
G is as defined above for ii;

(v) a group of the formula:

[R$_6$R$_5$N-G-N(R$_2$)- group]

where
R$_2$ and G are as defined above for iv and ii, respectively, and
R$_5$ and R$_6$ independently represent hydrogen, lower alkyl having 1–6 carbon atoms, cycloalkyl having 3–7 carbon atoms, —SO$_2$R$_8$ where R$_8$ is (C$_1$–C$_6$) alkyl, (C$_3$–C$_7$)cycloalkyl, or optionally substituted phenyl, or
R$_5$ and R$_6$ together with the nitrogen atom to which they are attached form a heterocyclic moiety such as imidazolyl, pyrrolidinyl, morpholinyl, piperazinyl, or piperidinyl;

(vi) a group of the formula:

[cyclic O-G-N-G group]

where G is as defined above for ii; or (vii) a group of the formula:

[cyclic R$_2$N-G-N-G group]

where each G is as defined above for ii; and

Y is
(viii) lower alkyl having 1–8 carbon atoms or cycloalkyl having 3–7 carbon atoms, any of which may be optionally substituted with one or more hydroxy, halogen, (C$_1$–C$_6$)alkoxy, alkoxyalkoxy where each alkoxy is (C$_1$–C$_6$)alkoxy, (C$_1$–C$_6$) alkylthio, (C$_3$–C$_7$)cycloalkylthio, aryl, heteroaryl, or mono- or di(C$_1$–C$_6$)alkylamino groups;

(ix) a group of the formula:

[-K-OR$_9$ group]

where K is lower alkylene having 1–6 carbon atoms optionally substituted with (C$_1$–C$_6$)alkyl or alkylene, or a cyclic group of the formula

[cyclic group with (CH)$_m$, K', and (CH$_2$)$_n$]

where K' independently represents hydrogen or (C$_1$–C$_6$) alkyl or alkylene, n is 0, 1, or 2, and m is an integer of from 1 to 5, with the proviso that the sum of n+m is not less than 1 or greater than 5; and R$_9$ is hydrogen, lower alkyl, or (C$_3$–C$_7$)cycloalkyl, where the alkyl or cycloalkyl is optionally substituted with halogen, lower alkoxy, or mono- or dialkylamino;

(x) a group of the formula:

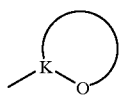

where K is defined as above in ix;

(xi) a group of the formula:

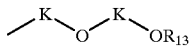

where

K is as defined above for ix, and $R_{13}$ is hydrogen, lower alkyl having 1–6 carbon atoms, or cycloalkyl having 3–7 carbon atoms, where the alkyl and cycloalkyl groups are optionally substituted with one or more $(C_1–C_6)$alkoxy or mono- or di$(C_1–C_6)$alkylamino groups; and (xii) a group of the formula:

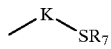

where

K is as defined above for ix, and $R_7$ is hydrogen, lower alkyl having 1–6 carbon atoms, or cycloalkyl having 3–7 carbon atoms; and (xiii) a group of the formula:

where

K is as defined above for ix; and $R_{14}$ and $R_{15}$ independently represent hydrogen, lower alkyl having 1–6 carbon atoms, cycloalkyl having 3–7 carbon atoms, —SO$_2$R$_8$ where R$_8$ is as defined above, or $R_{14}$ and $R_{15}$ together with the nitrogen atom to which they are attached form a heterocyclic moiety such as imidazolyl, pyrrolidinyl, morpholinyl, piperazinyl, or piperidinyl;

(xiv) a group of the formula:

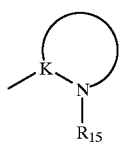

where K and $R_{15}$ are as defined above in ix and xii, respectively;

(xv) a group of the formula:

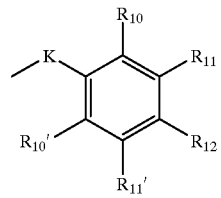

where

K is as defined above for ix;

$R_{10}$ and $R_{10}'$ are the same or different and are selected from hydrogen, $(C_1–C_6)$alkyl, halogen, hydroxy, lower alkoxy having 1–6 carbon atoms, or cycloalkoxy having 3–7 carbon atoms;

$R_{11}$, $R_{11}'$, and $R_{12}$ are the same or different and are selected from hydrogen, $C_1–C_6$ alkyl, halogen, hydroxy, —OR$_4$, —CR$_7$(R$_9$) NR$_5$R$_6$, —CR$_9$(R$_{16}$) OR$_4$, or $R_{11}$ and $R_{12}$ taken together with the atoms to which they are attached form a (hetero)cyclic ring; and $R_{16}$ is hydrogen, lower alkyl having 1–6 carbon atoms, or cycloalkyl having 3–7 carbon atoms;

(xvi) a group of the formula:

where K is as defined above for ix; and W is heteroaryl;

(xvii) a group of the formula:

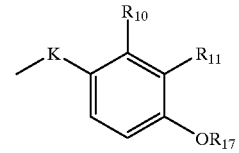

where

K is as defined above for ix; $R_{10}$ and $R_{11}$ are as defined above for xv, and $R_{17}$ is hydrogen, lower alkyl, or $(C_3–C_7)$cycloalkyl, where the alkyl or cycloalkyl is optionally substituted with halogen, lower alkoxy, or mono- or di$(C_1–C_6)$alkylamino;

(xviii) a group of the formula:

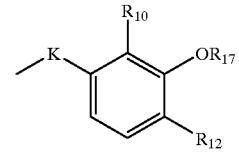

where K, $R_{10}$, $R_{12}$, and $R_{17}$ are as defined above;

(xix) a group of the formula:

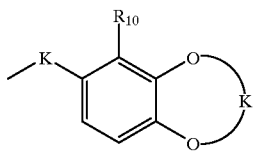

where each K is independently as defined above for ix and $R_{10}$ is defined above;

(xx) a group of the formula:

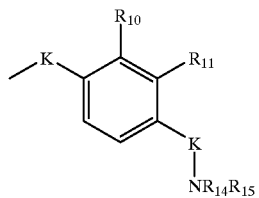

where K, $R_{10}$, $R_{11}$, $R_{14}$, and $R_{15}$ are as defined above;

(xxi) a group of the formula:

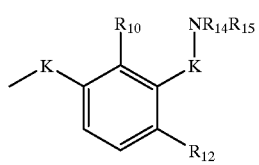

where K, $R_{10}$, $R_{12}$, $R_{14}$, and $R_{15}$ are as defined above;

(xxii) pyrimidinyl($C_1$–$C_6$)alkyl or pyridyl($C_1$–$C_6$)alkyl; or (xxiii) a group of the formula:

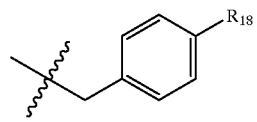

where $R_{18}$ represents hydrogen, amino, mono-, or di($C_1$–$C_6$)alkylamino, or $C_1$–$C_6$ alkyl optionally substituted with a $R_{19}$ where $R_{18}$ represents:

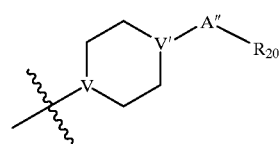

where
V and V' are independently CH or nitrogen;
A" is $C_1$–$C_6$ alkylene; and
$R_{20}$ is phenyl, pyridyl, or pyrimidinyl, each of which is optionally mono-, di-, or trisubstituted independently with halogen, hydroxy, $C_1$–$C_6$ alkoxy, amino, or mono- or di($C_1$–$C_6$)alkylamino.

Preferred pyrimidinyl($C_1$–$C_6$)alkyl Y groups are 2- and 4-pyrimidinylmethyl. Preferred pyridyl($C_1$–$C_6$)alkyl Y groups are 2- and 4-pyridylmethyl.

Preferred benzyl Y groups are those where $R_{18}$ is amino or a substituted methyl or ethyl group. More preferred $R_{18}$ substituents are piperazin-1-yl or piperidin-1-yl substituted at the 4-position with a halogenated benzyl group. Particularly preferred benzyl Y groups are 4-[1-[4-(4-Fluorobenzyl) piperazinyl]methyl]benzyl and 4-[1-[4-(4-Fluorobenzyl) piperidinyl]methyl]benzyl.

Preferred "X" groups in Formula IA are various quinolinyl, isoquinolinyl, tetrahydroquinolinyl or tetrahydroisoquinolinyl groups, e.g., groups of the formulas:

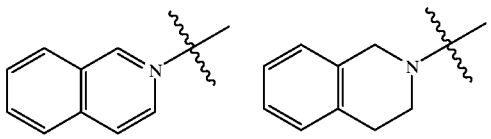

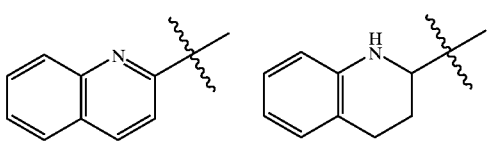

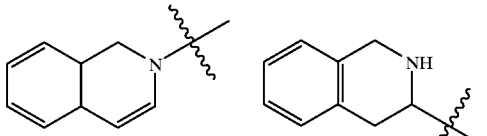

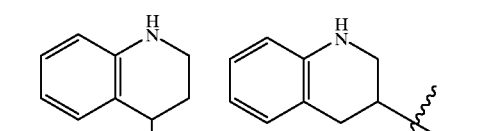

The following formulae are preferred embodiments of the invention:

II

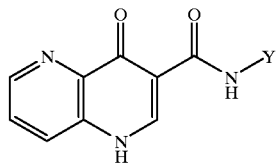

wherein Y is defined above.

III

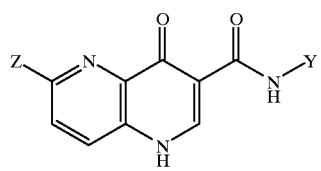

wherein Z represents halogen and Y is as defined above.

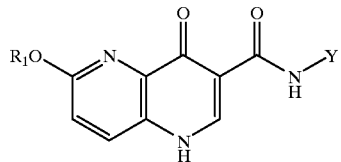
IV wherein $R_1$ and Y are defined above.

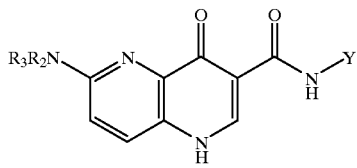
V wherein $R_2$, $R_3$, and Y are defined above.

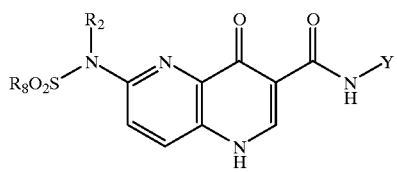
VI wherein $R_2$, $R_8$, and Y are defined above.

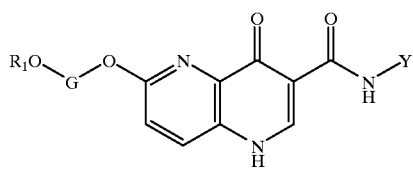
VII wherein $R_1$, G and Y are defined above.

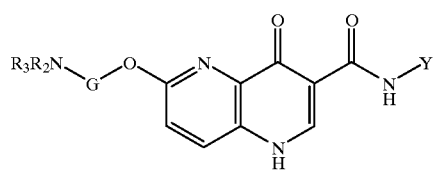
VIII wherein $R_2$, $R_3$, G, and Y are defined above.

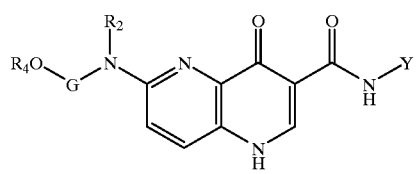
IX wherein $R_2$, $R_4$, G, and Y are defined above.

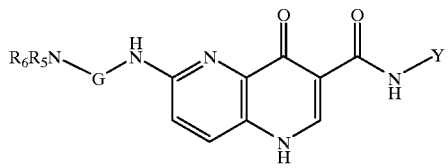
X wherein $R_2$, $R_5$, $R_6$, G, and Y are defined above.

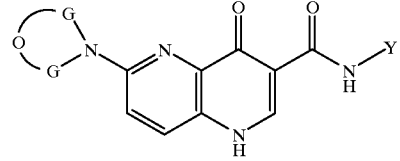
XI wherein G and Y are defined above.

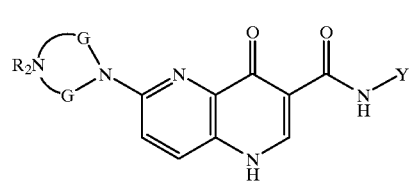
XII wherein $R_2$, G, and Y are defined above.

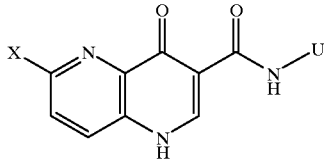
XIII wherein X is defined above and U is $(C_1-C_6)$lower alkyl or $(C_1-C_6)$cycloalkyl.

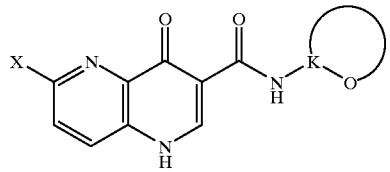
XIV wherein X, K, and $R_1$ are defined above.

XV wherein X and K are defined above.

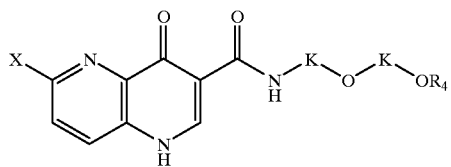
XVI wherein X, K, and R$_4$ are defined above.

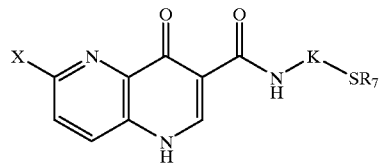
XVII wherein X, K, and R$_7$ are defined above.

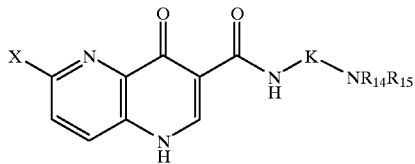
XVIII wherein X, K, R$_{14}$, and R$_{15}$ are defined above.

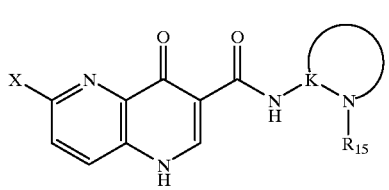
XIX wherein X, K, and R$_{15}$ are defined above.

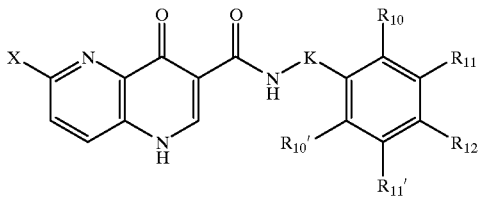
XX wherein:
R$_{10}$, R$_{10}$' are the same or different and may be selected from hydrogen, (C$_1$–C$_6$)alkyl, halogen, hydroxy, lower alkoxy having 1–6 carbon atoms, or cycloalkoxy having 3–7 carbon atoms;
R$_{11}$, R$_{11}$', and R$_{12}$ are the same or different and may be selected from hydrogen, (C$_1$–C$_6$)alkyl, halogen, hydroxy, —OR$_4$, —CR$_7$(R$_9$)N$_R$5R$_6$, —CR$_7$(R$_9$)OR$_4$; or
R$_{11}$ and R$_{12}$ taken together with the atoms to which they are attached form a (hetero)cyclic ring; and R$_9$ is as defined above.

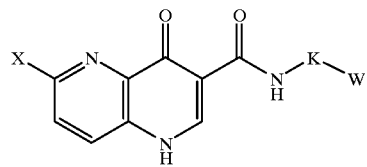
XXI wherein

X and K are defined above; and

W is heteroaryl.

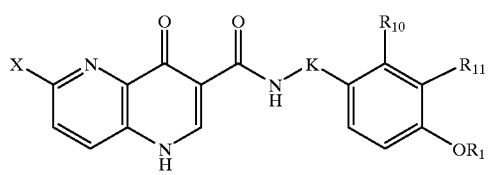
XXII wherein X, K, R$_1$, R$_{10}$, and R$_{11}$ are defined above.

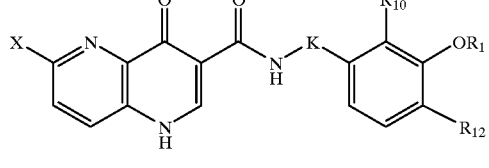
XXIII wherein X, K, R$_1$, R$_{10}$, and R$_{12}$ are defined above.

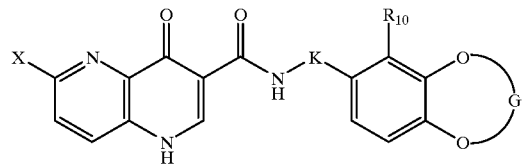
XXIV wherein X, K, and R$_{10}$ are defined above.

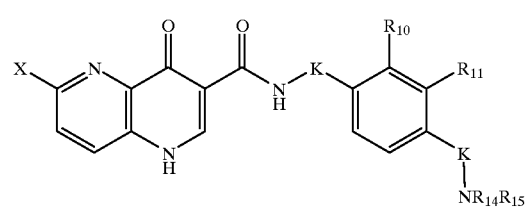
XXV wherein X, K, $R_{14}$, $R_{15}$, $R_{10}$, and $R_{11}$ are defined above.

Formula XXVI

Preferred compounds of the invention are encompassed by the following formulae:

Formula XXVII where

A is $C_1$–$C_6$ alkylene;

$R_a$ is phenyl optionally mono-, di-, or trisubstituted with halogen, lower alkyl, lower alkoxy, or mono- or di-$C_1$–$C_6$ alkylamino, or mono- or di-$C_1$–$C_6$ alkylamino lower alkyl; and $R_b$ is lower alkyl or lower cycloalkyl.

More preferred compounds of Formula XXVII are those where A is methylene, $R_a$ is phenyl optionally substituted with methyl or ethyl, and $R_b$ is lower alkyl. Particularly preferred compounds of Formula XXVII are those where A is methylene, $R_a$ is phenyl and $R_b$ is $C_1$–$C_3$ alkyl.

Formula XXVIII wherein

A is $C_1$–$C_6$ alkylene;

$R_a$ and $R_a'$ are independently phenyl groups optionally mono-, di-, or trisubstituted with halogen, lower alkyl, lower alkoxy, or mono- or di-$C_1$–$C_6$ alkylamino, or mono- or di-$C_1$–$C_6$ alkylamino lower alkyl; and $R_c$ is hydrogen or lower alkyl.

More preferred compounds. of Formula XXVIII are those where A is methylene, $R_a$ and $R_a'$ are independently phenyl optionally substituted with methyl or ethyl, and $R_c$ is lower alkyl. Particularly preferred compounds of Formula XXVII are those where A is methylene, $R_a$ is phenyl substituted in the para position with lower alkyl, $R_a'$ is phenyl, and $R_c$ is $C_1$–$C_3$ alkyl.

Formula XXIX wherein

A is $C_1$–$C_6$ alkylene;

$R_d$ and $R_e$ are independently lower alkyl groups.

More preferred compounds of Formula XXIX are those where A is $C_2$–$C_4$ alkylene. Particularly preferred compounds of Formula XXIX are those where A is $C_2$–$C_4$ alkylene, $R_d$ is $C_1$–$C_3$ alkyl, and $R_e$ is $C_2$–$C_4$ alkyl.

Formula XXX wherein

A is $C_1$–$C_6$ alkylene;

$R_d$ is lower alkyl; and $R_f$ is a group of the formula:

where

E is oxygen or nitrogen; and

M is $C_1$–$C_3$ alkylene or nitrogen.

More preferred compounds of Formula XXX are those where A is $C_1$—$C_3$ alkylene. Still more preferred compounds of Formula XXX are those where A is $C_2$–$C_4$ alkylene, $R_d$ is $C_1$–$C_3$ alkyl, and $R_e$ is $C_2$–$C_4$ alkyl. Particularly preferred compounds of Formula XXX are those where A is $C_2$–$C_4$ alkylene, $R_d$ is $C_1$–$C_3$ alkyl, $R_e$ is $C_2$–$C_4$ alkyl, and E is nitrogen and M is methylene, E is oxygen and M is methylene or ethylene, or E and M are both nitrogen.

Other preferred compounds of Formula XXX are those where $R_f$ is furanyl, tetrahydrofuranyl, or imidazolyl.

Formula XXXI wherein

A is $C_1$–$C_6$ alkylene;

$R_d$ is lower alkyl optionally substituted with amino or mono- or di($C_1$–$C_6$)alkylamino; and $R_a'$ is phenyl optionally mono-, di-, or trisubstituted with halogen, lower alkyl, lower alkoxy, or mono- or di-$C_1$-$C_6$ alkylamino, or mono- or di-$C_1$-$C_6$ alkylamino lower alkyl.

More preferred compounds of Formula XXXI are those where A is $C_1$-$C_3$ alkylene, $R_a'$ is phenyl optionally substituted with methyl or ethyl, and $R_d$ is $C_1$-$C_3$ alkyl. Still mere preferred compounds of Formula XXXI are where A is methylene, $R_a'$ is phenyl optionally substituted with methyl or ethyl, and $R_d$ is $C_3$-$C_6$ alkyl. Particularly preferred compounds of Formula XXXI are sodium, potassium, or ammonium salts of the corresponding parent compound.

Other preferred compounds of Formula XXXI are those where $R_a'$ is phenyl substituted with mono- or di-($C_1$-$C_6$) alkylamino lower alkyl.

Formula XXXIa

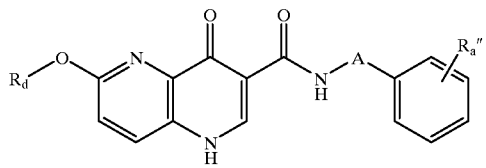

wherein

A is $C_1$-$C_6$ alkylene;

$R_d$ is lower alkyl; and $R_a''$ is phenyl, pyridyl, imidazolyl, pyrimidinyl, or pyrrolyl, each of which is optionally substituted with up to two groups selected from halogen, lower alkyl, lower alkoxy, mono- or di($C_1$-$C_6$)alkylamino, or mono- or di-$C_1$-$C_6$ alkylamino lower alkyl.

More preferred compounds of Formula XXXIa are those where $R_a''$ is imidazolyl and $R_d$ is $C_1$-$C_3$ alkyl. Still more preferred compounds of Formula XXXI are where A is methylene, $R_a''$ is imidazolyl, and $R_d$ is $C_3$-$C_6$ alkyl.

Formula XXXII

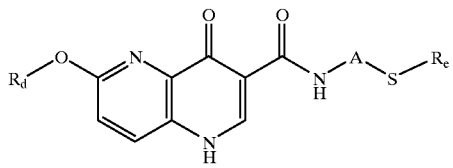

wherein

A is $C_1$-$C_5$ alkylene; and $R_d$ and $R_e$ are independently lower alkyl groups.

More preferred compounds of Formula XXXII are those where A is $C_1$-$C_3$ alkylene. Particularly preferred compounds of Formula XXXII are those where A is $C_1$-$C_3$ alkylene, $R_d$ is $C_1$-$C_3$ alkyl, and $R_e$ is $C_1$-$C_3$ alkyl.

Formula XXXIII

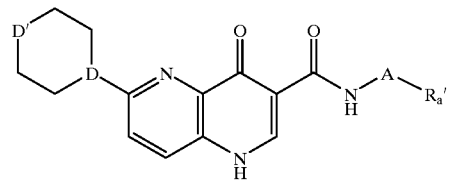

wherein

D is nitrogen or CH;

D' is nitrogen or oxygen;

A is $C_1$-$C_6$ alkylene; and $R_a'$ is phenyl, pyridyl, or thiazolyl, each of which is optionally mono-, di-, or trisubstituted with halogen, lower alkyl, lower alkoxy, or mono- or di-$C_1$-$C_6$ alkylamino, or mono- or di-$C_1$-$C_6$ alkylamino lower alkyl.

More preferred compounds of Formula XXXIII are those where A is $C_1$-$C_3$ alkylene, $R_a'$ is phenyl optionally substituted with lower alkyl or halogen, and D is nitrogen. Still more preferred compounds of Formula XXXIII are where A is methylene, $R_a'$ is phenyl optionally substituted, with lower alkyl or halogen, D is nitrogen, and D' is oxygen.

Formula XXXIV

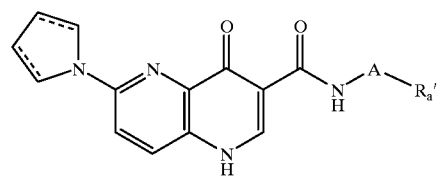

wherein

A is $C_1$—$C_6$ alkylene; and $R_a'$ is hydrogen;

$R_a'$ is thienyl or phenyl, each of which is optionally mono-, di-, or trisubstituted with halogen, lower alkyl, lower alkoxy, or mono- or di-$C_1$-$C_6$ alkylamino, or mono- or di-$C_1$-$C_6$ alkylamino lower alkyl.

More preferred compounds of Formula XXXIV are those where A is $C_1$-$C_3$ alkylene, and $R_a'$ is phenyl optionally substituted with lower alkyl or halogen. Still more preferred compounds of Formula XXXIV are where A is methylene, $R_a'$ is phenyl optionally substituted with lower alkyl, lower alkoxy or halogen.

Formula XXXV

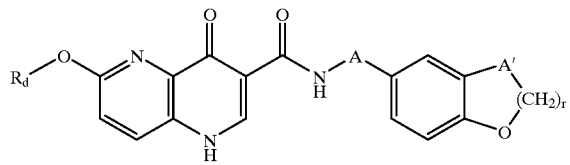

wherein

A is $C_1$-$C_6$ alkylene; and $R_d$ is lower alkyl;

A' represents oxygen or methylene; and r is an integer of from 1–3.

More preferred compounds of Formula XXXV are those where A is $C_1-C_3$ alkylene. Particularly preferred compounds of Formula XXXV are those where A is $C_1-C_3$ alkylene, and $R_d$ is $C_1-C_3$ alkyl.

Formula XXXVa

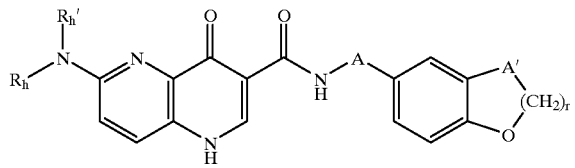

wherein

A is $C_1-C_6$ alkylene; and $R_h$ and $R_h'$ are independently hydrogen or lower alkyl, where each alkyl is optionally substituted with lower alkoxy;

A' represents oxygen or methylene; and r is an integer of from 1–3.

More preferred compounds of Formula XXXVa are those where A is $C_1-C_3$ alkylene. Particularly preferred compounds of Formula XXXV are those where A is $C_1-C_3$ alkylene, and $R_h$ is $C_1-C_3$ alkyl.

Formula XXXVI

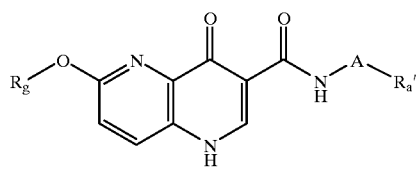

wherein

A is $C_1-C_6$ alkylene;

$R_g$ is lower alkoxy lower alkyl; and $R_a'$ is phenyl optionally mono-, di-, or trisubstituted with halogen, lower alkyl, lower alkoxy, or mono- or di-$C_1-C_6$ alkylamino, or mono- or di-$C_1-C_6$ alkylamino lower alkyl.

Formula XXXVII

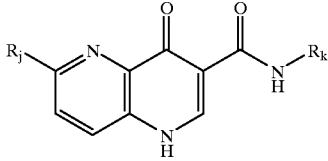

wherein $R_j$ is halogen or lower alkoxy; and $R_k$ is lower alkyl or cycloalkyl each of which is optionally substituted with hydroxy, lower alkyl, or lower alkoxy; or $R_k$ is phenyl ($C_1-C_6$) alkyl where the phenyl group is optionally mono-, di-, or trisubstituted with halogen, lower alkyl, lower alkoxy, or mono- or di-$C_1-C_6$ alkylamino, or mono- or di-$C_1-C_6$ alkylamino lower alkyl.

Formula XXXVIII

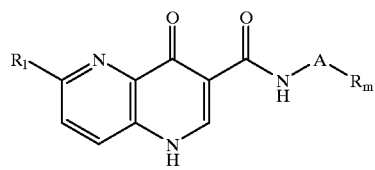

wherein

A is $C_1-C_6$ alkylene;

$R_l$ is lower alkoxy, benzyloxy, lower alkoxy lower alkoxy, amino, or mono- or di-($C_1-C_6$)alkylamino; and $R_m$ is pyranyl, dihydropyranyl, tetrahydropyranyl, or hexahydropyranyl, pyridine, dihydropyridine, tetrahydropyridine, or piperidine.

Preferred compounds of Formula XXXVIII are those where $R_l$ is lower alkoxy and $R_m$ is tetrahydropyranyl.

Formula XXXIX

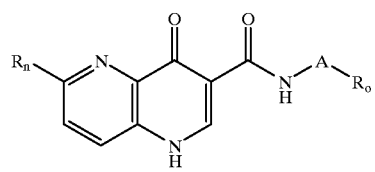

wherein

A is $C_1-C_6$ alkylene;

$R_n$ is lower alkoxy, lower alkoxy lower alkoxy, benzyl, or a group of the formula:

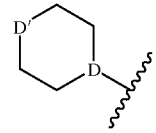

where

D is nitrogen or CH; and

D' is nitrogen or oxygen; and $R_o$ is pyranyl, 2- or 3-thienyl; or $R_o$ is 2-, 4-, or 5-thiazolyl or 2-, 4-, or 5-imidazolyl, each of which may be optionally substituted with lower alkyl.

Preferred compounds of Formula XXXIX are those where

Formula XXXX

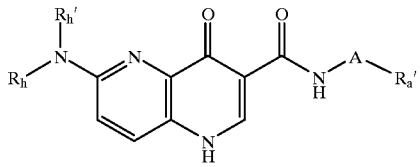

wherein

A is $C_1-C_6$ alkylene;

$R_h$ and $R_h'$ are independently hydrogen or lower alkyl, where each lower alkyl is optionally substituted with lower alkoxy; and $R_a'$ is phenyl optionally mono-, di-, or trisubstituted with halogen, lower alkyl, lower alkoxy, or mono- or di-$C_1$–$C_6$ alkylamino, or mono- or di-$C_1$–$C_6$ alkylamino lower alkyl; or $R_a'$ is thienyl optionally substituted with lower alkyl.

Formula XXXXI

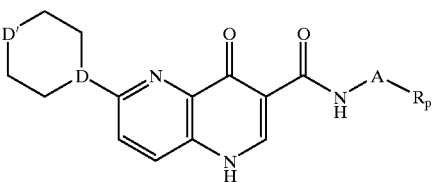

wherein
A is $C_1$–$C_6$ alkylene;
D is nitrogen or CH;
D' is nitrogen or oxygen; and
$R_p$ is lower alkyl or lower alkyl optionally substituted with lower alkoxy.

Formula XXXXII

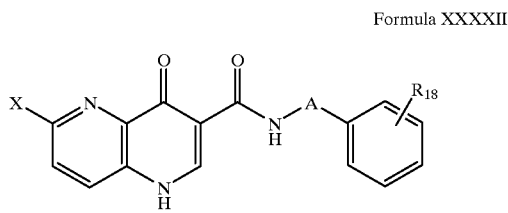

wherein
A is $C_1$–$C_6$ alkylene;
X is defined as above for Formula I; and
$R_{18}$ is
(i) amino or mono- or di($C_1$–$C_6$)alkylamino; or
(ii) lower alkyl optionally substituted with

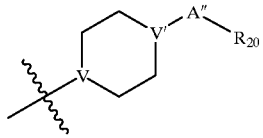

where
V and V' are independently CH or nitrogen;
A" is $C_1$–$C_6$ alkylene; and
$R_{20}$ is phenyl, pyridyl, or pyrimidinyl, each of which is optionally mono-, di-, or trisubstituted independently with halogen, hydroxy, $C_1$–$C_6$ alkoxy, amino, or mono- or di($C_1$–$C_6$)alkylamino.

More preferred compounds of Formula XXXXII are those where V is nitrogen and X is $C_1$–$C_6$ alkoxy or $C_1$–$C_6$ alkyl optionally substituted with up to three halogen atoms. Particularly preferred compounds of XXXXII are those where V and V' are nitrogen; X is $C_1$–$C_3$ alkoxy or $C_1$–$C_3$ alkyl optionally substituted with up to three halogen atoms; A" is methylene or ethylene; and $R_{20}$ is halogenated phenyl. A preferred $R_{20}$ group is 4-fluorophenyl. Highly preferred compounds of XXXXII are those where X is 2,2,2-trifluoroethyl; V and V' are nitrogen; $R_{20}$ is halogenated phenyl; and A and A' are methylene or ethylene.

In certain situations, compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable acid and base addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts, of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)$n-ACOOH where n is 0–4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By lower alkyl in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By cycloalkyl in the present invention is meant cycloalkyl groups having 3–7 atoms such as, for example cyclopropyl, cyclobutyl, cyclopentyl, cyclohexyl, and cycloheptyl.

By aryl is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy.

By lower alkoxy in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By cycloalkoxy in the present invention is meant cycloalkylalkoxy groups having 3–7 carbon atoms where cycloalkyl is defined above.

By halogen in the present invention is meant fluorine, bromine, chlorine, and iodine.

By heteroaryl (aromatic heterocycle) in the present invention is meant one or more aromatic ring systems of 5-, 6-, or 7-membered rings containing at least one and up to four hetero atoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, naphthyridinyl, benzimidazolyl, and benzoxazolyl.

Specific examples of heteroaryl groups are the following:

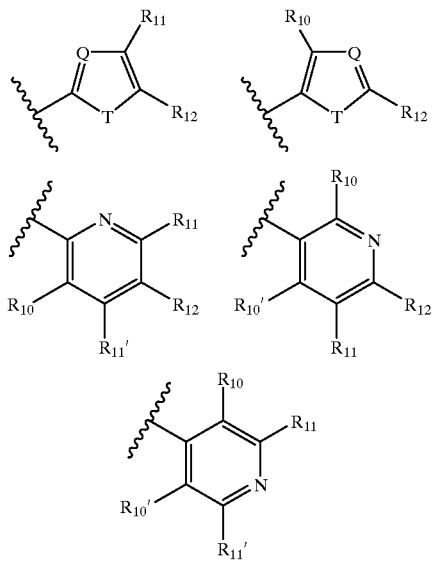

wherein

Q is nitrogen or —$CR_9$;

T is —$NR_7$, oxygen, or sulfur; and $R_9$, $R_{10}$, $R_{10}'$, $R_{11}$, $R_{11}'$, $R_{12}$ are as defined above.

Where Y represents a carbocyclic group, it is attached to the amide nitrogen by a single bond. The result s an amide of the formula:

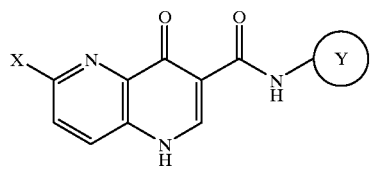

where X is defined as above and

represents the Y carbocyclic group.

Where X is a carbocyclic group, such moiety or group includes both aromatic heterocycles (heteroaryl), unsaturated heterocyclic ring systems, and saturated heterocyclic ring systems. Examples of such groups are imidazolyl, pyrrolidinyl, morpholinyl, piperazinyl, or piperidinyl. Preferred X carbocyclic groups are linked to the parent naphthyridine moiety by a nitrogen atom in the X carbocyclic group. Thus, for example, when pyrrolidinyl is the X carbocyclic group, it is preferably a 1-pyrrolidinyl group of the formula:

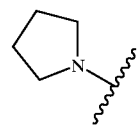

Where Y is a carbocyclic group, such moiety or group includes both aromatic heterocycles (heteroaryl groups), unsaturated heterocyclic ring systems, and saturated heterocylic ring systems. Examples of such groups are imidazolyl, pyrrolidinyl, morpholinyl, piperazinyl, or piperidinyl. Preferred Y carbocyclic groups are linked to the parent naphthyridine carboxamide group by a nitrogen atom in the Y carbocyclic group. Thus, for example, when piperidinyl is the Y carbocyclic group, it is preferably a 1-piperidinyl group of the formula:

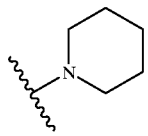

By "optionally substituted phenyl" as used herein is meant phenyl groups that are unsubstituted or substituted with up to 3 groups selected independently from halogen, hydroxy, lower alkyl, lower alkoxy, trifluoromethyl, and mono- or di-lower alkylamino.

Representative compounds of the invention are shown below in Table 1.

TABLE 1

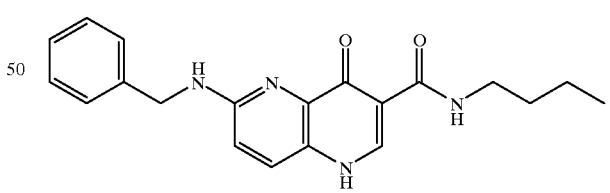

Compound 1

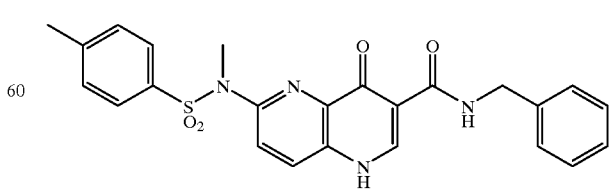

Compound 2

TABLE 1-continued

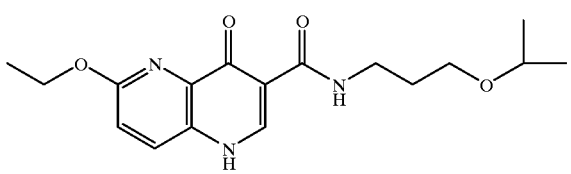

Compound 3

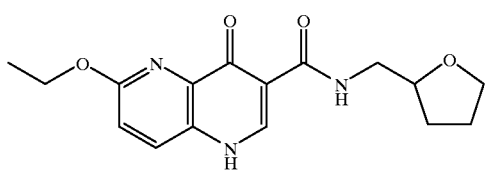

Compound 4

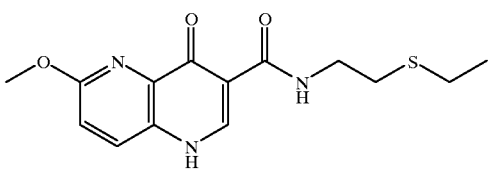

Compound 5

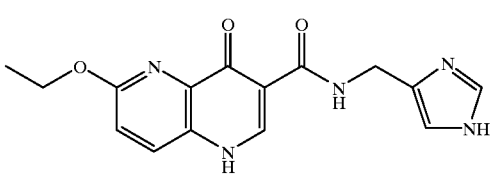

Compound 6

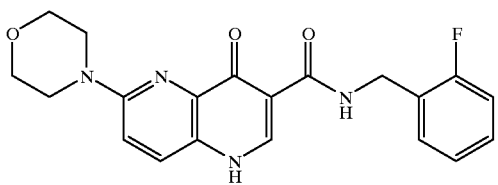

Compound 7

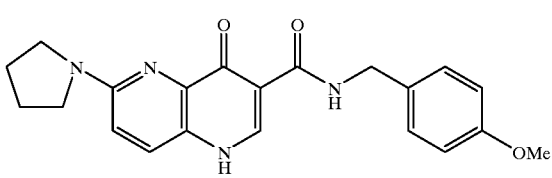

Compound 8

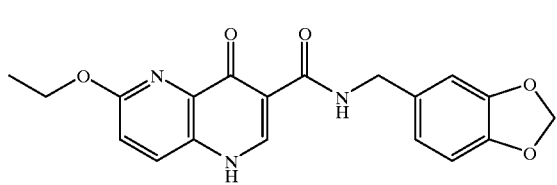

Compound 9

TABLE 1-continued

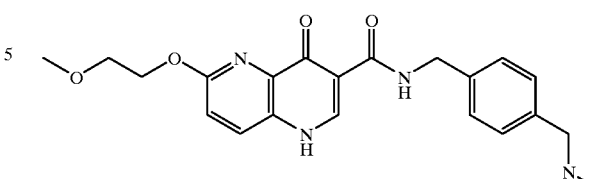

Compound 10

The pharmaceutical utility of compounds of this invention is indicated by the following assays for GABAa receptor activity.

Assays are carried out as described in Thomas and Tallman (J. Bio. Chem. 156: 9838–9842, J. Neurosci. 3: 433–440, 1983). Rat cortical tissue is dissected and homogenized in 25 volumes (w/v) of 0.05 M Tris HCl buffer (pH 7.4 at 4° C.). The tissue homogenate is centrifuged in the cold (4°) at 20,000×g for 20'. The supernatant is decanted and the pellet is rehomogenized in the same volume of buffer and again centrifuged at 20,000×g. The supernatant is decanted and the pellet is frozen at −20° C. overnight. The pellet is then thawed and rehomogenized in 25 volume (original wt/vol) of buffer and the procedure is carried out twice. The pellet is finally resuspended in 50 volumes (w/vol of 0.05 M Tris HCl buffer (pH 7.4 at 40° C.).

Incubations contain 100 ml of tissue homogenate, 100 ml of radioligand 0.5 nM ($^3$H-Ro15-1788 [$^3$H-Flumazenil] specific activity 80 Ci/mmol), drug or blocker and buffer to a total volume of 500 ml. Incubations are carried for 30 min at 4° C. then are rapidly filtered through GFB filters to separate free and bound ligand. Filters are washed twice with fresh 0.05 M Tris HCl buffer (pH 7.4 at 4° C.) and counted in a liquid scintillation counter. 1.0 mM diazepam is added to some tubes to determine nonspecific binding. Data are collected in triplicate determinations, averaged and % inhibition of total specific binding is calculated. Total Specific Binding=Total−Nonspecific. In some cases, the amounts of unlabeled drugs is varied and total displacement curves of binding are carried out. Data are converted to $K_i$'s. Compounds of the invention when tested in the assay described above have $K_i$'s of less than 1 μM.

In addition, the following assay may be used to determine if the compounds of the invention are agonists, antagonists, or inverse agonists, and, therefore, their specific pharmaceutical utility. The following assay can be employed to determine specific GABAa receptor activity.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Xenopus Laevis oocytes are enzymatically isolated and injected with non-polyadenylated cRNA mixed in a ratio of 4:1:4 for human derived α, β, and γ subunits, respectively. For each subunit combination, sufficient message is injected to result in current amplitudes of >10 nA when 1 μM GABA is applied.

Electrophysiological recordings are carried out using the two electrode voltage-clamp technique at a membrane holding potential of −70 mV.

Compounds are evaluated against a GABA concentration that evokes <10% of the maximal evokable GABA current. Each oocyte is exposed to increasing concentrations of compound in order to evaluate a concentration/effect relationship. Compound efficacy is expressed as a percent-change in current amplitude: $100*((Ic/I)-1)$, where Ic is the GABA evoked current amplitude observed in the presence of compound and I is the GABA evoked current amplitude observed in the absence of compound.

Specificity of a compound for the Ro15-1788 site is determined following completion of the concentration/effect curve. After washing the oocyte sufficiently to remove previously applied compound, the oocyte is exposed to GABA+1 μM Ro15-1788, followed by exposure to GABA+1 μM Ro15-1788+compound. Percent change due to addition of compound is calculated as described above. Any percent change observed in the presence of Ro15-1788 is subtracted from the percent changes in current amplitude observed in the absence of 1 μM Ro15-1788. These net values are used for the calculation of average efficacy and $EC_{50}$ values.

To evaluate average efficacy and $EC_{50}$ values, the concentration/effect data are averaged across cells and fit to the logistic equation. Average values are reported as mean±standard error.

The substituted 4-oxo-napthyridine-3-carboxamides of Formula I and their salts are suitable for the diagnosis and treatment of anxiety, Down Syndrome, sleep, cognitive and seizure disorders, and overdose with benzodiazepine drugs and for enhancement of alertness, both in human and non-human animals and domestic pets, especially dogs and cats and farm animals such as sheep, swine and cattle.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the species of the host animal to be treated, the particular mode of administration, and the body weight of the host. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It will be convenient to formulate these animal feed and drinking water compositions with a mullet-dose of the drug so that the animal takes in an appropriate quantity of the composition along with its diet. It will also be convenient to present the composition as a premix for addition to the feed or drinking water.

An illustration of the preparation of compounds of the present invention is given in Scheme I.

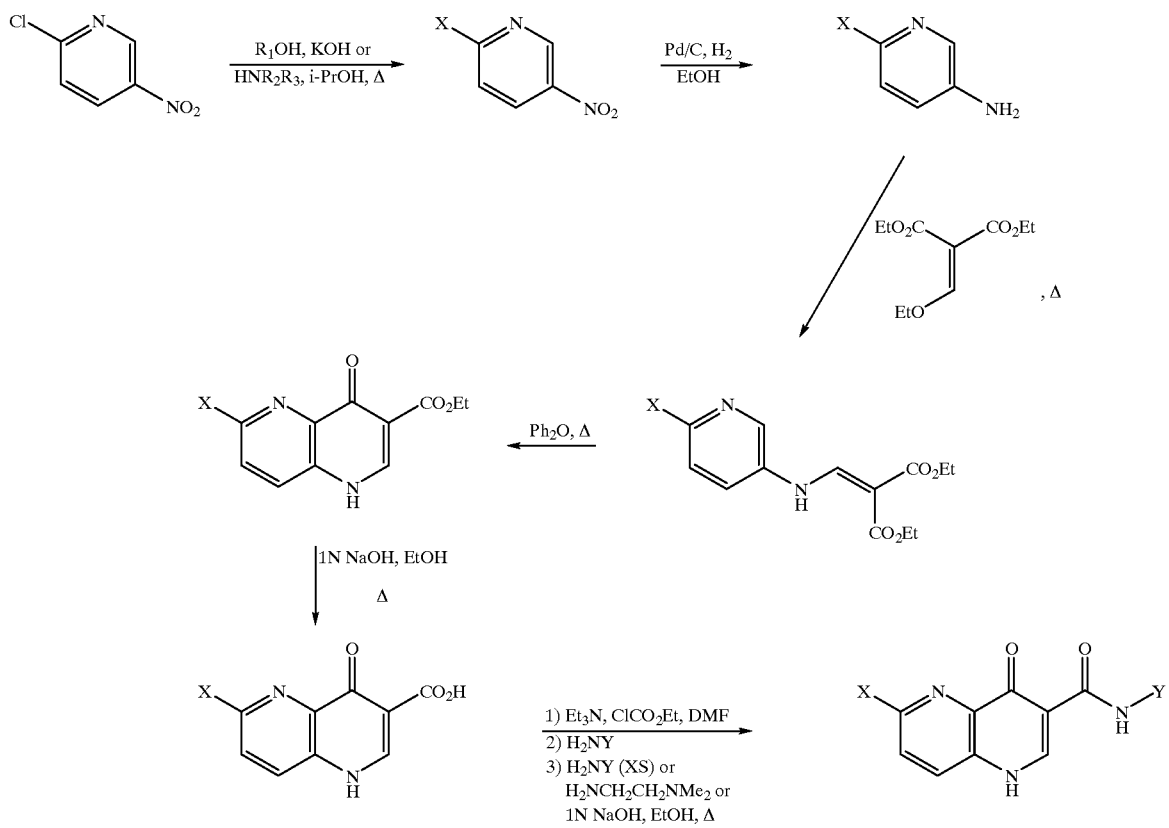

Scheme I

In Scheme I, the substituents X and Y carry the definitions set forth above for formula I.

Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, the need for such protecting groups will be apparent to those skilled in the art of organic synthesis as well as the conditions necessary to attach and remove such groups.

The invention is illustrated further by the following examples which are not to be construed as limiting the invention in scope or spirit to the specific procedures described in them.

EXAMPLE 1

Preparation of Starting Materials and Intermediates

The starting materials and various intermediates may be obtained from commercial sources, prepared from commercially available organic compounds, or prepared using well known synthetic methods.

Representative examples of methods for preparing intermediates of the invention are set forth below.

1. 2-Benzylamino-5-nitropyridine

A solution of 2-chloro-5-nitropyridine (1.59 g, 10 mmol) and benzylamine (2.3 mL, 21 mmol) in ethanol (10 mL) was heated at reflux for 2 h. The reaction mixture was allowed to ambient temperature, 1.2 N HCl was added, the precipitate collected, rinsed with water, and dried to give 2.02 g of 2-benzylamino-5-nitropyridine as a yellow solid.

2. 2-Benzylamino-5-aminopyridine

A mixture of 2-benzylamino-5-nitropyridine (2.02 g) and 10% Pd/C (202 mg) in ethanol (20 mL) was placed in a Paar bottle and shaken under hydrogen (50 PSI) for 3 h. The mixture was filtered through Celite using dichloromethane and concentrated in vacuo to afford 1.76 g of 2-benzylamino-5-aminopyridine as a burgundy oil.

3. Diethyl(2-benzylamino-5-pyridylaminomethylene)malonate

A mixture of 2-benzylamino-5-aminopyridine (1.76 g) and diethyl ethoxymethylenemalonate (1.78 mL, 8.82 mmol) was heated at 130° C. for 2 h. While warm, the mixture was evacuated. After cooling, the product was triturated with 2:1 hexanes/ether and collected to give 2.74 g of diethyl (2-benzylamino-5-pyridylaminomethylene) malonate as a gold solid.

4. Ethyl 6-benzylamino-4-oxo-1,4-dihydro-1,5-naphthyridine-3-carboxylate

Diethyl (2-benzylamino-5-pyridylaminomethylene) malonate (2.23 g) was added to diphenyl ether (10 mL) preheated to 230° C. Heating was continued for 0.5 h, the reaction flask removed from the oil bath, and the mixture allowed to cool to ambient temperature. The product was triturated with 1:1 ether:hexanes, collected, rinsed with ether, and dried to give 1.47 g of ethyl 6-benzylamino-4-oxo-1,4-dihydro-1,5-naphthyridine-3-carboxylate as a brown solid.

5. 6-Benzylamino-4-oxo-1,4-dihydro-1,5-naphthyridine-3-carboxylic acid

A mixture of ethyl 6-benzylamino-4-oxo-1,4-dihydro-1,5-naphthyridine-3-carboxylate (60 mg), 1N NaOH (2 mL), and ethanol (0.5 mL) was heated at reflux for 2 h. The reaction mixture was cooled in an ice bath and saturated aqueous ammonium chloride was added. The resulting precipitate was collected, rinsed with water and ether, then dried to afford 35 mg of 6-benzylamino-4-oxo-1,4-dihydro-1,5-naphthyridine-3-carboxylic acid as a brown solid.

6. 2-Ethoxy-5-nitropyridine

2-Chloro-5-nitropyridine was added to a homogeneous solution of potassium hydroxide (3.93 g, 70 mmol) in ethanol (35 mL) at ambient temperature. The reaction mixture was stirred for 1 h, then diluted with saturated aqueous ammonium chloride and cooled in an ice bath. The precipitate was collected, rinsed with water and dried to give 3.60 g of 2-ethoxy-5-nitropyridine as a beige solid.

7. 2-Ethoxy-5-aminopyridine

A mixture of 2-ethoxy-5-nitropyridine (3.60 g) and 10% Pd/C (360 mg) in ethanol (40 mL) was placed in a Paar bottle and shaken under hydrogen (50 PSI) for 16 h. The mixture was filtered through Celite using dichloromethane and concentrated to give 2.892 g of 2-ethoxy-5-aminopyridine as a gold solid.

8. Diethyl (2-ethoxy-5-pyridylaminomethylene) malonate

A mixture of 2-ethoxy-5-aminopyridine (2.89 g, 20.9 mmol) and diethyl ethoxymethylenemalonate (4.23 mL, 20.9 mmol) was heated at 130° C. for 4.5 hours. While warm, the mixture was evacuated. After cooling, the product was triturated with 2:1 hexanes:ether and collected to afford 6.04 g of diethyl (2-ethoxy-5-pyridylaminomethylene) malonate as a beige solid.

9. Ethyl 6-ethoxy-4-oxo-1,4-dihydro-1,5-naphthyridine-3-carboxylate

Diethyl (2-ethoxy-5-pyridylaminomethylene)malonate (6.04 g) was added to diphenyl ether (20 mL) preheated to 230° C. Heating was continued for 0.5 h, the reaction flask removed from the oil bath, and the mixture allowed to cool to ambient temperature. The product was triturated with 1:1 ether:hexanes, collected, rinsed with ether, and dried to give 2.98 g of ethyl 6-ethoxy-4-oxo-1,4-dihydro-1,5-naphthyridine-3-carboxylate as a tan solid.

10. 6-Ethoxy-4-oxo-1,4-dihydro-1,5-naphthyridine-3-carboxylic acid

A mixture of ethyl 6-ethoxy-4-oxo-1,4-dihydro-1,5-naphthyridine-3-carboxylate (2.98 g), 1N NaOH (50 mL), and ethanol (10 mL) was heated at reflux for 2 h. The reaction mixture was cooled in an ice bath, acidified, and the resulting precipitate collected, rinsed with water and dried to give 2.42 g of 6-ethoxy-4-oxo-1,4-dihydro-1,5-naphthyridine-3-carboxylic acid as a beige solid.

11. 4-[(n-tert-Butoxycarbonyl)methylaminomethyl) benzylamine hydrochloride a) A solution of α-bromo-p-tolunitrile (4.90 g, 25 mmol) in acetonitrile (50 mL) was added dropwise to a stirring solution of 40% aqueous methylamine (21.5 mL, 250 mmol) in acetonitrile (50 mL) at 0° C. The reaction mixture was stirred 0.5 h, then concentrated in vacuo. Water was added to the residue and extracted 2× with dichloromethane. The combined organic layers were dried over sodium sulfate, filtered, and concentrated in vacuo to give 1.41 g of 4-(methylaminomethyl) benzonitrile as a yellow oil containing ~30% of N,N-bis(4-benzonitrile)methyl-amine. The, aqueous was adjusted to pH>8 and extracted 2× with 9:1 dichloromethane:methanol. The combined extracts were dried over sodium sulfate, filtered, and concentrated in vacuo to give 1.13 g of pure 4-(methylamino) benzonitrile as a colorless oil.

b) Di-tert-butyl dicarbonate (1.77 g, 8.1 mmol) was added to a stirring mixture of 4-(methylaminomethyl)

benzonitrile (1.13 g, 7.7 mmol) and 1N NaOH (15 mL) in 1,4-dioxane (15 mL) at ambient temperature. The reaction mixture was stirred for 2 h, poured into saturated aqueous sodium chloride, and extracted with dichloromethane. The organic layer was dried over sodium sulfate, filtered, and concentrated in vacuo to give 1.81 g of crude 4-{N-(tert-butoxycarbonyl)-methylaminomethyl]benzonitrile. The crude material was filtered through a 1" silica gel pad, first eluting with hexane, then with ether. The ether filtrate was concentrated to give pure 4-{N-(tert-butoxycarbonyl)-methylaminomethyl]benzonitrile as a colorless oil. To this was added 10% Pd/C (170 mg) and ethanol in a Paar bottle. The mixture was shaken under hydrogen (50 PSI) for 4.5 h, then a filtered through Celite and concentrated in vacuo. The residue was taken up in ethanol, cooled in an ice bath, and 1.0 M HCl in ether (10 mL) was added dropwise. The resulting precipitate was filtered and dried in a vacuum oven to give 1.346 g of 4-[(N-tert-butoxycarbonyl)-methylaminomethyl) benzylamine hydrochloride as a pale gray solid.

EXAMPLE 2

1. N-n-Butyl-6-benzylamino-4-oxo-1,4-dihydro-1,5-naphthyridine-3-carboxamide

To a solution of 6-benzylamino-4-oxo-1,4-dihydro-1,5-naphthyridine-3-carboxylic acid (59 mg, 0.2 mmol) and triethylamine (59 ml, 0.42 mmol) in N,N-dimethylformamide (1 mL) at 0° C. was added ethyl chloroformate (39 mL, 0.41 mmol). After stirring at 0° C. for 1 h, n-butylamine 99 mL, 1.0 mmol) was added. The reaction mixture was stirred an additional 2 h at 0° C., then poured into saturated aqueous sodium chloride. The mixture was cooled in an ice bath, the precipitate collected, rinsed with water and ether, then dried to afford 49 mg of N-n-butyl 6-benzylamino-4-oxo-1,4-dihydro-1,5-naphthyridine-3-carboxamide as a brown solid. Compound 1. An alternate name for this compound is: N-butyl(4-oxo-6-(benzylamino) (3-hydro-5-azaquinolyl))formamide.

2. N-[2-(Ethylthio)ethyl] 6-methoxy-4-oxo-1,4-dihydro-1,5-napththyridine-3-carboxamide To a solution of 6-methoxy-4-oxo-1,4-dihydro-1,5-naphthyridine-3-carboxylic acid (55 mg, 0.25 mmol) and triethylamine (73 mL, 0.53 mmol) in N,N-dimethylformamide (2 mL) at 0° C. was added ethyl chloroformate (49 mL, 0.52 mmol). After stirring at 0° C. for 0.5 h, 2-(ethylthio)ethylamine hydrochloride (172 mg, 1 mmol) and triethylamine (139 ml, 1 mmol) was added. The reaction mixture was stirred for 0.5 h at 0° C., then poured into 1.2 N HCl, cooled in an ice bath, and the resulting precipitate collected, rinsed with water and dried to give 57 mg of N-[2-(ethylthio)ethyl] 6-methoxy-4-oxo-1,4-dihydro-1,5-napththyridine-3-carboxamide as a beige solid; m.p. 257–259° C. (d). Compound 5.

3. N-[4-(Methylaminomethyl)benzyl] 6-(2-methoxyethoxy)-4-oxo-1,4-dihydro-1,5 naphthyridine-3-carboxamide hydrochloride To a solution of 6-(2-methoxyethoxy)-4-oxo-1,4-dihydro-1,5-naphthyridine-3-carboxylic acid (106 mg, 0.4 mmol) and triethylamine (117 mL, 0.84 mmol) in 4:1 tetrahydrofuran: N,N-dimethylformamide (2 mL) at 0° C. was added ethyl chloroformate (66 mL, 0.82 mmol). After stirring at 0° C. for 1.25 h, 4-[(N-tert-butoxycarbonyl)-methylaminomethyl)benzylamine hydrochloride (120 mg, 0.42 mmol) and triethylamine (59 mL, 0.42 mmol) was added. The reaction mixture was stirred at 0° C. for 0.75 h, then allowed to ambient temperature and stirred for 20 h. N,N-Dimethylethylenediamine (132 mL, 1.2 mmol) was added, the reaction mixture stirred for 1 h, then concentrated in vacuo. The residue was cooled in an ice bath, saturated aqueous ammonium chloride was added and the mixture extracted with dichloromethane. The organic layer was washed with saturated aqueous sodium chloride, dried over sodium sulfate, filtered, and concentrated to give 177 mg of crude N-[4-(N-tert butoxycarbonyl)-methylaminomethyl) benzyl] 6-(2-methoxyethoxy)-4-oxo-1,4-dihydro-1,5-naphthyridine-3-carboxamide.

To crude N-[4-(N-tert-butoxycarbonyl)-methylaminomethyl)benzyl] 6-(2-methoxyethoxy)-4-oxo-1, 4-dihydro-1,5-naphthyridine-3-carboxamide in dichloromethane (1 mL) was added 1:1 trifluoroacetic acid:dichloromethane (2 mL) dropwise at ambient temperature. The reaction mixture was stirred for one hour, concentrated in vacuo, the residue dissolved in ethanol, and 1.0M HCl in ether (0.8 mL) was added. The precipitate was collected to afford 68 mg of N-[4-(methylaminomethyl) benzyl] 6-(2-methoxyethoxy)-4-oxo-1,4-dihydro-1,5-naphthyridine-3-carboxamide hydrochloride. Compound 10.

4. N-(4-Methoxybenzyl) 6-pyrrolidino-4-oxo-1,4-dihydro-1,5-naphthyridine-3-carboxamide To a solution of 6-pyrrolidino-4-oxo-1,4-dihydro-1,5-naphthyridine-3-carboxylic acid (80 mg, 0.3 mmol) and triethylamine (0.11 mL, 0.8 mmol) in 5:1 tetrahydrofuran: N,N-dimethylformamide (6 mL) at 0° C. was added ethyl chloroformate (0.09 mL, 0.9 mmol). After stirring at 0° C. for 0.5 h, 4-methoxybenzylamine (0.1 mL, 0.8 mmol) was added. The reaction mixture was allowed to ambient temperature and stirred for 0.5 h. Water was added and the resulting precipitate collected, washed with water and ether and dried. The solid was combined with 1N NaOH (5 mL) and ethanol (2 mL) and heated at reflux for 0.25 h. The reaction mixture was cooled in in ice bath, 3N HCl was added to achieve pH 8, and the precipitate collected, rinsed with water and ether and dried to give 69 mg of N-(4-methoxybenzyl) 6-pyrrolidino-4-oxo-1,4-dihydro-1,5-naphthyri-dine-3-carboxamide; m.p. 270–272° C. Compound 8.

5a. N-Benzyl 6-ethoxy-4-oxo-1,4-tetrahydro-1,5-napthyridine-3-carboxamide, sodium salt N-Benzyl 6-ethoxy-4-oxo-1,4-tetrahydro-1,5-napthyridine-3-carboxamide (914 mg, 2.83 mmol) is suspended in ethyl alcohol (9 mL) and 10 N NaOH (0.27 mL) is added. The mixture is heated until homogenous, subsequently, cooled and concentrated. The resulting solid is treated with ethyl acetate (5 mL) and ethyl alcohol (250 mL), and the resulting mixture is stirred for 22 h. The precipitate is collected, rinsed with ethyl acetate and dried to give the sodium salt of N-benzyl 6-ethoxy-4-oxo-1,4-tetrahydro-1,5-napthyridine-3-carboxamide (Compound 12) (960 mg) as a tan solid.

5b. N-benzyl 6-ethoxy-4-oxo-1,4-tetrahydro-1,5-napthyridine-3-carboxamide, potassium salt; (Compound 13) m.p. 286–288° C.

EXAMPLE 3

The following compounds were prepared essentially according to the procedures described in Examples 1–2:

(a) N-n-Butyl 6-chloro-4-oxo-1,4-tetrahydro-1,5-naphthyridine-3-carboxamide; (Compound 14) m.p. 330° C. (d).
(b) N-Propan-3-ol 6-methoxy-4-oxo-1,4-tetrahydro-1,5-naphthyridine-3-carboxamide; (Compound 15) m.p. 241–272° C.
(c) N-n-Butyl 6-ethoxy-4-oxo-1,4-tetrahydro-1,5-naphthyridine-3-carboxamide; (Compound 16) m.p. 274–276° C.
(d) N-(2-Ethylthio)ethyl 6-methoxy-4-oxo-1,4-tetrahydro-1,5-naphthyridine-3-carboxamide; (Compound 17) m.p. 257–259° C.
(e) N-n-Butyl 6-(N-benzylamino)-4-oxo-1,4-tetrahydro-1,5-naphthyridine-3-carboxamide (Compound 18).
(f) N-n-Pentyl 6-ethoxy-4-oxo-1,4-tetrahydro-1,5-naphthyridine-3-carboxamide; (Compound 19) m.p.265–265° C.
(g) N-(3-Isopropoxy)propyl 6-ethoxy-4-oxo-1,4-tetrahydro-1,5-naphthyridine-3-carboxamide (Compound 20).
(h) N-Benzyl 6-ethoxy-4-oxo-1,4-tetrahydro-1,5-naphthyridine-3-carboxamide; (Compound 21) m.p.275–278° C.
(i) N-2-Pentyl 6-ethoxy-4-oxo-1,4-tetrahydro-1,5-naphthyridine-3-carboxamide (Compound 22).
(j) N-(2-Tetrahydrofuranyl)methyl 6-ethoxy-4-oxo-1,4-tetrahydro-1,5-naphthyridine-3-carboxamide; m.p.235–237° C. (Compound 4).
(k) N-(3-Methoxy)propan-2-ol 6-ethoxy-4-oxo-1,4-tetrahydro-1,5-naphthyridine-3-carboxamide (Compound 23).
(l) N-(3-Methoxy)propyl 6-ethoxy-4-oxo-1,4-tetrahydro-1,5-naphthyridine-3-carboxamide (Compound 24).
(m) N-(2-Methoxy)ethyl 6-ethoxy-4-oxo-1,4-tetrahydro-1,5-naphthyridine-3-carboxamide (Compound 25).
(n) N-Isoamyl 6-ethoxy-4-oxo-1,4-tetrahydro-1,5-naphthyridine-3-carboxamide; (Compound 26) m.p. 279–281° C.
(o) N-(2-Furanyl)methyl 6-ethoxy-4-oxo-1,4-tetrahydro-1,5-naphthyridine-3-carboxamide; (Compound 27) m.p. 245 (d)° C.
(p) N-(3-Methoxybenzyl) 6-ethoxy-4-oxo-1,4-tetrahydro-1,5-naphthyridine-3-carboxamide; m.p. 250–253° C. (Compound 11).
(q) N-(3-Ethoxy)propyl 6-ethoxy-4-oxo-1,4-tetrahydro-1,5-naphthyridine-3-carboxamide; (Compound 28) m.p. 224–225° C.
(r) N-2-(2-Methyl)butyl 6-ethoxy-4-oxo-1,4-tetrahydro-1,5-naphthyridine-3-carboxamide; (Compound 29) m.p. 282–283° C.
(s) N-2-Pentan-1-ol 6-ethoxy-4-oxo-1,4-tetrahydro-1,5-naphthyridine-3-carboxamide; (Compound 30) m.p. 232–234° C.
(t) N-5-Pentanol 6-ethoxy-4-oxo-1,4-tetrahydro-1,5-naphthyridine-3-carboxamide; (Compound 31) m.p. 223–224° C.
(u) N-1-Cyclohexan-2-ol 6-ethoxy-4-oxo-1,4-tetrahydro-1,5-naphthyridine-3-carboxamide; (Compound 32) m.p.268–270° C.
(v) N-Benzyl 6-methoxy-4-oxo-1,4-tetrahydro-1,5-naphthyridine-3-carboxamide; (Compound 33) m.p. 273–274° C.
(w) N-(2-Fluorobenzyl) 6-methoxy-4-oxo-1,4-tetrahydro-1,5-naphthyridine-3-carboxamide; (Compound 34) m.p. 266–271° C.
(x) N-(3-Fluorobenzyl) 6-methoxy-4-oxo-1,4-tetrahydro-1,5-naphthyridine-3-carboxamide; (Compound 35) m.p.281° C.
(y) N-(4-Fluorobenzyl) 6-methoxy-4-oxo-1,4-tetrahydro-1,5-naphthyridine-3-carboxamide; (Compound 36) m.p.283–286° C.
(z) N-(Imidazol-4-ylmethyl) 6-ethoxy-4-oxo-1,4-tetrahydro-1,5-naphthyridine-3-carboxamide. (Compound 6). [Alternate name: (6-ethoxy-4-oxo(3-hydro-5-azaquinolyl))-N-(imidazol-4-ylmethyl)formamide]
(aa) N-4-Tetrahydropyranyl 6-ethoxy-4-oxo-1,4-tetrahydro-1,5-naphthyridine-3-carboxamide; (Compound 37) m.p.303–305° C.
(bb) N-(3-Thienyl)methyl 6-ethoxy-4-oxo-1,4-tetrahydro-1,5-naphthyridine-3-carboxamide; (Compound 38) m.p.324–325° C.
(cc) N-2-(6-Methyl)heptan-6-ol 6-ethoxy-4-oxo-1,4-tetrahydro-1,5-naphthyridine-3-carboxamide; (Compound 39) m.p.281° C.
(dd) N-(2-Tetrahydropyranyl)methyl 6-ethoxy-4-oxo-1,4-tetrahydro-1,5-naphthyridine-3-carboxamide; (Compound 40) m.p.204–206° C.
(ee) N-(2-Fluorobenzyl) 6-ethoxy-4-oxo-1,4-tetrahydro-1,5-naphthyridine-3-carboxamide; (Compound 41) m.p. 157–162° C.
(ff) N-(3-Fluorobenzyl) 6-ethoxy-4-oxo-1,4-tetrahydro-1,5-naphthyridine-3-carboxamide; (Compound 42) m.p. 297–302° C.
(gg) N-(4-Fluorobenzyl) 6-ethoxy-4-oxo-1,4-tetrahydro-1,5-naphthyridine-3-carboxamide (Compound 43).
(hh) N-(4-Methoxybenzyl) 6-ethoxy-4-oxo-1,4-tetrahydro-1,5-naphthyridine-3-carboxamide; (Compound 44) m.p. 186° C.
(ii) N-(3-Fluorobenzyl) 6-methoxy-4-oxo-1,4-tetrahydro-1,5-naphthyridine-3-carboxamide; (Compound 45) m.p.301° C.
(jj) N-Benzyl 6-(N-methyl, N-toluenesulfonyl-amino)-4-oxo-1,4-tetrahydro-1,5-naphthyridine-3-carboxamide. (Compound 2). [Alternate name: (6-(methyl((4-methylphenyl)sulfonyl)amino)-4-oxo(3-hydro-5-azaquinolyl))-N-benzylformamide]
(kk) N-Benzyl 6-(methylamino)-4-oxo-1,4-tetrahydro-1,5-naphthyridine-3-carboxamide (Compound 46).
(ll) N-Piperonyl 6-ethoxy-4-oxo-1,4-tetrahydro-1,5-naphthyridine-3-carboxamide; m.p.190° C. (Compound 9).
(mm) N-Piperonyl 6-methoxy-4-oxo-1,4-tetrahydro-1,5-naphthyridine-3-carboxamide; (Compound 47) m.p.186° C.
(nn) N-2-(Imidazol-4-ylethyl) 6-ethoxy-4-oxo-1,4-tetrahydro-1,5-naphthyridine-3-carboxamide; (Compound 48) m.p.268° C.
(oo) N-(4-Methylbenzyl) 6-ethoxy-4-oxo-1,4-tetrahydro-1,5-naphthyridine-3-carboxamide; (Compound 49) m.p.270–271° C.
(pp) N-Benzyl 6-(2-methoxyethoxy)-4-oxo-1,4-tetrahydro-1,5-naphthyridine-3-carboxamide; (Compound 50) m.p.>300° C.
(qq) N-Benzyl 6-dimethylamino-4-oxo-1,4-tetrahydro-1,5-naphthyridine-3-carboxamide; (Compound 51) m.p.246–249° C.
(rr) N-Isoamyl 6-morpholino-4-oxo-1,4-tetrahydro-1,5-naphthyridine-3-carboxamide; (Compound 52) m.p.295–298° C.
(ss) N-Benzyl 6-morpholino-4-oxo-1,4-tetrahydro-1,5-naphthyridine-3-carboxamide; (Compound 53) m.p. 88–90° C.
(tt) N-(2-Fluorobenzyl) 6-morpholino-4-oxo-1,4-tetrahydro-1,5-naphthyridine-3-carboxamide; m.p.137–139° C. (Compound 7).

(uu) N-(3-Ethoxy)propyl 6-morpholino-4-oxo-1,4,-tetrahydro-1,5-naphthyridine-3-carboxamide; (Compound 54) m p.150–152° C.
(vv) N-n-Butyl 6-morpholino-4-oxo-1,4-tetrahydro-1,5-naphthyridine-3-carboxamide; (Compound 55) m.p.275–277° C.
(ww) N-(2-Pyridyl)methyl 6-morpholino-4-oxo-1,4-tetrahydro-1,5-naphthyridine-3-carboxamide; (Compound 56) m.p.125–127° C.
(xx) N-(2-Thienyl)methyl 6-(2-methoxyethoxy)-4-oxo-1,4-tetrahydro-1,5-naphthyridine-3-carboxamide; (Compound 57) m.p.235–236° C.
(yy) N-Isoamyl 6-dimethylamino-4-oxo-1,4-tetrahydro-1,5-naphthyridine-3-carboxamide; (Compound 58) m.p. 254–256° C.
(zz) N-(2-Thienyl)methyl 6-morpholino-4-oxo-1,4-tetrahydro-1,5-naphthyridine-3-carboxamide; (Compound 59) m.p.277–279° C.
(aaa) N-(2-Thienyl)methyl 6-dimethylamino-4-oxo-1,4-tetrahydro-1,5-naphthyridine-3-carboxamide; (Compound 60) m.p. 240° C.
(bbb) N-(2-Thiazolyl)methyl 6-morpholino-4-oxo-1,4-tetrahydro-1,5-naphthyridine-3-carboxamide; (Compound 61) m.p.270–272° C.
(ccc) N-(4-Methylaminomethyl)benzyl 6-ethoxy-4-oxo-1,4-tetrahydro-1,5-naphthyridine-3-carboxamide (Compound 62).
(ddd) N-[4-(1-Methylamino)ethyl]benzyl 6-ethoxy-4-oxo-1,4-tetrahydro-1,5-naphthyridine-3-carboxamide; (Compound 63) m.p. 259–262° C.
(eee) N-(2-Tetrahydrofuranyl)methyl 6-dimethylamino-4-oxo-1,4-tetrahydro-1,5-naphthyridine-3-carboxamide; (Compound 64) m.p. 285–288° C.
(fff) N-n-Pentyl 6-morpholino-4-oxo-1,4-tetrahydro-1,5-naphthyridine-3-carboxamide; (Compound 65) m.p.278–280° C.
(ggg) N-(3-Methoxybenzyl) 6-morpholino-4-oxo-1,4-tetrahydro-1,5-naphthyridine-3-carboxamide; (Compound 66) m.p.204–205° C.
(hhh) N-(3-Fluorobenzyl) 6-morpholino-4-oxo-1,4-tetrahydro-1,5-naphthyridine-3-carboxamide; (Compound 67) m.p.263–265° C.
(iii) N-(4-Methylaminomethyl)benzyl 6-(2-methoxyethoxy)-4-oxo-1,4-tetrahydro-1,5-naphthyridine-3-carboxamide; (Compound 68) m.p. 275–277° C.
(jjj) N-n-Butyl 6-pyrrolidino-4-oxo-1,4-tetrahydro-1,5-naphthyridine-3-carboxamide; (Compound 69) m.p.57–58° C.
(kkk) N-(4-Methoxybenzyl) 6-pyrrolidino-4-oxo-1,4-tetrahydro-1,5-naphthyridine-3-carboxamide; (Compound 70) m.p.270–272° C.
(lll) N-(2-Thienyl)methyl 6-pyrrolidino-4-oxo-1,4-tetrahydro-1,5-naphthyridine-3-carboxamide; (Compound 71) m.p.265–267° C.
(mmm) N-[4-(1-Methylamino)ethyl]benzyl 6-dimethylamino-4-oxo-1,4-tetrahydro-1,5-naphthyridine-3-carboxamide (Compound 72).
(nnn) N-(4-Methylaminomethyl)benzyl 6-n-propoxy-4-oxo-1,4-tetrahydro-1,5-naphthyridine-3-carboxamide hydrochloride; (Compound 73) m.p.270–271° C.
(ooo) N-[4-(1-Methylamino)ethyl]benzyl 6-chloro-4-oxo-1,4-tetrahydro-1,5-naphthyridine-3-carboxamide; (Compound 74) m.p.260–263° C.
(ppp) N-[4-(1-Methylamino)ethyl]benzyl 6-pyrrolidino-4-oxo-1,4-tetrahydro-1,5-naphthyridine-3-carboxamide hydrochloride; (Compound 75) m.p.298–302° C.
(qqq) N-(4-Ethoxybenzyl) 6-morpholino-4-oxo-1,4-tetrahydro-1,5-naphthyridine-3-carboxamide; (Compound 76) m.p.278–281° C.
(rrr) N-(4-Ethoxybenzyl) 6-pyrrolidino-4-oxo-1,4-tetrahydro-1,5-naphthyridine-3-carboxamide; (Compound 77) m.p.265–267° C.
(sss) N-(4-Chlorobenzyl) 6-morpholino-4-oxo-1,4-tetrahydro-1,5-naphthyridine-3-carboxamide; (Compound 78) m.p.295–297° C.
(ttt) N-(3-Chlorobenzyl) 6-morpholino-4-oxo-1,4-tetrahydro-1,5-naphthyridine-3-carboxamide; (Compound 79) m.p.276–278° C.
(uuu) N-Piperonyl 6-dimethylamino-4-oxo-1,4-tetrahydro-1,5-naphthyridine-3-carboxamide hydrochloride; (Compound 80) m.p.246–247° C.
(vvv) N-Benzyl 6-(2-methylamino)ethoxy-4-oxo-1,4-tetrahydro-1,5-naphthyridine-3-carboxamide (Compound 81).
(www) N-Benzyl 6-(2-dimethylamino)ethoxy-4-oxo-1,4-tetrahydro-1,5-naphthyridine-3-carboxamide; (Compound 82) m.p.194–198° C.
(xxx) N-(4-Ethylaminomethyl)benzyl 6-ethoxy-4-oxo-1,4-tetrahydro-1,5-naphthyridine-3-carboxamide; (Compound 83) m.p.194° C. (d).
(yyy) N-Benzyl 6-(2-methoxy)ethylamino-4-oxo-1,4-tetrahydro-1,5-naphthyridine-3-carboxamide; (Compound 84) m.p.254–257° C.
(zzz) N-(3-Methylaminomethyl)benzyl 6-ethoxy-4-oxo-1,4-tetrahydro-1,5-naphthyridine-3-carboxamide hydrochloride; (Compound 85) m.p.187° C. (d).
(aaaa) N-(4-Dimethylaminomethyl)benzyl 6-ethoxy-4-oxo-1,4-tetrahydro-1,5-naphthyridine-3-carboxamide hydrochloride; (Compound 86) m.p.200° C. (d).
(bbbb) N-(3-Methylaminomethyl)benzyl 6-n-propoxy-4-oxo-1,4-tetrahydro-1,5-naphthyridine-3-carboxamide hydrochloride (Compound 87) m.p.184° C. (d).
(cccc) N-[4-(1-Imidazolylmethy)]benzyl 6-ethoxy-4-oxo-1,4-tetrahydro-1,5-naphthyridine-3-carboxamide; (Compound 88) m.p.143–145° C.
(dddd) N-[4-(1-morpholinomethyl)]benzyl 6-ethoxy-4-oxo-1,4-tetrahydro-1,5-napthyridine-3-carboxamide; (Compound 89) m.p. 215–218° C.
(eeee) N-[3-(1-morpholinomethyl)]benzyl 6-ethoxy-4-oxo-1,4-tetrahydro-1,5-naphthyridine-3-carboxamide; (Compound 90) m.p. 195–198° C.
(ffff) N-{4-[1-(4-methylpiperazinomethyl)]benzyl 6-ethoxy-4-oxo-1,4-tetrahydro-1,5-napthyridine-3-carboxamide (Compound 91).
(gggg) N-[4-(1,2,4-triazol-1-ylmethyl)]benzyl 6-ethoxy-4-oxo-1,4-tetrahydro-1,5-napthyridine-3-carboxamide; (Compound 92) m.p.195–200° C.
(hhhh) N-Benzyl 6-benzylamino-4-oxo-1,4-tetrahydro-1,5-naphthyridine-3-carboxamide (Compound 93).
(iiii) N-Cyclohexyl 6-ethoxy-4-oxo-1,4-tetrahydro-1,5-naphthyridine-3-carboxamide (Compound 94).
(jjjj) N-Cyclohexylmethyl 6-ethoxy-4-oxo-1,4-tetrahydro-1,5-naphthyridine-3-carboxamide (Compound 95).
(kkkk) N-(4-Aminobenzyl)-6-ethoxy-4-oxo-1,4-tetrahydro-1,5-naphthyridine-3-carboxamide (Compound 96).
(llll) N-(4-Pyridylmethyl) 6-ethoxy-4-oxo-1,4-tetrahydro-1,5-naphthyridine-3-carboxamide (Compound 97).
(mmmm) N-Benzyl 6-tetrahydrolsoquinolinyl-4-oxo-1,4-tetrahydro-1,5-naphthyridine-3-carboxamide (Compound 98).
(nnnn) N-{4-[1-[4-(4-Fluorobenzyl)piperazinyl]methyl] benzyl} 6-(2,2,2-trifluoroethyl)-4-oxo-1,4-tetrahydro-1,5-naphthyridine-3-carboxamide, (Compound 99) m.p. 234–236° C.

(oooo) N-(3-isopropoxypropyl) 6-ethoxy-4-oxo-1,4-tetrahydro-1,5-naphthyridine-3-carboxamide Compound 3 [alternative name: (6-ethoxy-4-oxohydropyridino[3,2-b]pyridin-3-yl)-N-[3-(methylethoxy)propyl]carboxamide].

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A pharmaceutical composition comprising a compound of Formula I, or a pharmaceutically acceptable salt thereof, and a pharmaceutically acceptable carrier, wherein:

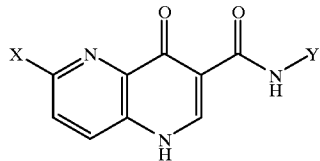

Formula I

X is hydrogen, halogen, —OR$_1$, C$_1$–C$_6$ alkyl optionally substituted with up to three groups selected independently from halogen and hydroxy, and —NR$_2$R$_3$;

X is phenyl, naphthyl, 1-(5,6,7,8-tetrahydro)naphthyl or 4-(1,2-dihydro)indenyl, pyridinyl, pyrimidyl, isoquinolinyl, 1,2,3,4-tetrahydroisoquinolinyl, benzofuranyl, or benzothienyl, each of which is optionally substituted with up to three groups selected from halogen, C$_1$–C$_6$ alkyl, C$_1$–C$_4$ alkoxy, C$_1$–C$_6$ alkylthio, hydroxy, amino, mono or di(C$_1$–C$_6$)alkylamino, cyano, nitro, trifluoromethyl and trifluoromethoxy; or X represents a carbocyclic group containing from 3–7 members, up to two of which members are optionally hetero atoms selected from oxygen and nitrogen, where the X carbocyclic group is optionally substituted with one or more groups selected from halogen, C$_1$–C$_6$ alkoxy, mono- or di (C$_1$–C$_6$)alkylamino, sulfonamide, aza(C$_3$–C$_7$) cycloalkyl, C$_3$–C$_7$ cycloalkylthio, C$_1$–C$_6$ alkylthio, phenylthio, or a heterocyclic group;

Y is lower alkyl having 1–8 carbon atoms optionally substituted with up to two groups selected from halogen, C$_3$–C$_7$ cycloalkyl, C$_1$–C$_6$ alkoxy, mono- or di(C$_1$–C$_6$)alkylamino, sulfonamide, aza(C$_3$–C$_7$) cycloalkyl, C$_3$–C$_7$ cycloalkylthio, C1–C$_6$ alkylthio, phenylthio, a heterocyclic group, —OR$_4$,—NR$_5$R$_6$, SR$_7$, and optionally substituted aryl; or Y is a carbocyclic group having from 3–7 members atoms, where up to three of which members are optionally hetero atoms selected from oxygen and nitrogen and where any member of the Y carbocyclic group is optionally substituted with halogen, —OR$_4$, —NR$_5$R$_6$, SR$_7$, aryl or a heterocyclic group;

R$_1$ is hydrogen, lower alkyl having 1–6 carbon atoms, or cycloalkyl having 3–7 carbon atoms, where each alkyl is optionally substituted with —OR$_4$, or —NR$_5$R$_6$;

R$_2$ and R$_3$ are the same or different and represent hydrogen, lower alkyl optionally mono- or disubstituted with alkoxy, aryl, or halogen;

aryl or aryl(C$_1$–C$_6$)alkyl where each aryl is optionally substituted with up to three groups selected from halogen, hydroxy, C$_1$–C$_6$ alkyl, C$_1$–C$_6$ alkoxy, or mono- or di (C$_1$–C$_6$) alkylamino;

cycloalkyl having 3–7 carbon atoms optionally mono or disubstituted with halogen, or alkoxy; or —SO$_2$R$_8$;

R$_4$ is as defined for R$_1$;

R$_5$ and R$_6$ carry the same definitions as R$_2$ and R$_3$, respectively;

R$_7$ is hydrogen, lower alkyl having 1–6 carbon atoms, or cycloalkyl having 3–7 carbon atoms; and R$_8$ is lower alkyl having 1–6 carbon atoms, cycloalkyl having 3–7 carbon atoms, or optionally substituted phenyl.

2. A pharmaceutical composition comprising a compound of Formula IA, or a pharmaceutically acceptable salt thereof, and a pharmaceutically acceptable carrier, wherein:

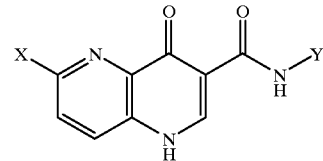

Formula IA

X is (i) hydrogen, halogen, mono- or dialkylamino, alkoxy, (ii) a group of the formula:

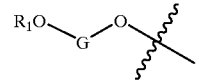

where G is lower alkylene having 1–6 carbon atoms, or a cyclic group of the formula

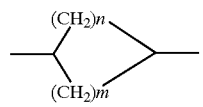

where n is 0, 1, or 2, and m is an integer of from 1 to 5, with the proviso that the sum of n+m is not greater than 5; and R$_1$ is hydrogen, lower alkyl, or (C$_3$–C$_7$)cycloalkyl, where each alkyl or cycloalkyl is optionally substituted with halogen, lower alkoxy, or mono- or di(C$_1$–C$_6$)alkylamino;

(iii) a group of the formula:

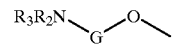

where

G is as defined above for ii; and

R$_2$ and R$_3$ independently represent hydrogen, lower alkyl having 1–6 carbon atoms, cycloalkyl having 3–7 carbon atoms, —SO$_2$R$_8$ where R$_8$ is (C$_1$–C$_6$) alkyl, (C$_3$–C$_7$)cycloalkyl, or optionally substituted phenyl, or $R_2$ and $R_3$ together with the nitrogen atom to which they are attached form a heterocyclic moiety selected from imidazolyl, pyrrolidinyl, morpholinyl, piperazinyl, and piperidinyl;

(iv) a group of the formula:

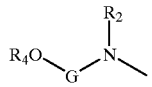

where $R_2$ is as defined above for iii;

$R_4$ is hydrogen, lower alkyl having 1–6 carbon atoms, or cycloalkyl having 3–7 carbon atoms, and may be optionally substituted with one or more $(C_1-C_6)$alkoxy or mono- or di$(C_1-C_6)$ alkylamino groups; and G is as defined above for ii;

(v) a group of the formula:

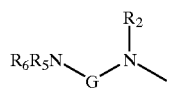

where $R_2$ and G are as defined above for iii and ii, respectively, and $R_5$ and $R_6$ independently represent hydrogen, lower alkyl having 1–6 carbon atoms, cycloalkyl having 3–7 carbon atoms, —$SO_2R_8$ where $R_8$ is $(C_1-C_6)$ alkyl, $(C_3-C_7)$cycloalkyl, or optionally substituted phenyl, or $R_5$ and $R_6$ together with the nitrogen atom to which they are attached form a heterocyclic moiety;

(vi) a group of the formula:

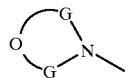

where G is as defined above for ii; or (vii) a group of the formula:

where G is as defined above for ii and $R_2$ is as defined above for iii; and

Y is (viii) lower alkyl having 1–8 carbon atoms or cycloalkyl having 3–7 carbon atoms, any of which is optionally substituted with one or more halogen, $(C_1-C_6)$ alkoxy, alkoxyalkoxy where each alkoxy is $(C_1-C_6)$alkoxy, $(C_1-C_6)$alkylthio, $(C_3-C_7)$ cycloalkylthio, aryl, heteroaryl, or mono- or di$(C_1-C_6)$alkylamino groups;

(ix) a group of the formula:

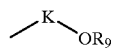

where K is lower alkylene having 1–6 carbon atoms optionally substituted with $(C_1-C_6)$alkyl or alkylene, or a cyclic group of the formula

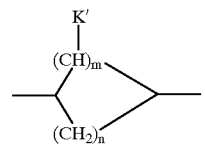

where K' independently represents hydrogen or $(C_1-C_6)$alkyl or alkylene, n is 0, 1, or 2, and m is an integer of from 1 to 5, with the proviso that the sum of n+m is not greater than 5; and $R_9$ is hydrogen, lower alkyl, or $(C_3-C_7)$cycloalkyl, where the alkyl or cycloalkyl is optionally substituted with halogen, lower alkoxy, or mono- or dialkylamino;

(x) a group of the formula:

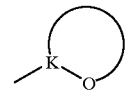

where K is defined as above in ix;

(xi) a group of the formula:

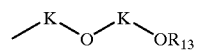

where

K is as defined above for ix, and $R_{13}$ is hydrogen, lower alkyl having 1–6 carbon atoms, or cycloalkyl having 3–7 carbon atoms, where the alkyl and cycloalkyl groups are optionally substituted with one or more $(C_1-C_6)$alkoxy or mono- or di$(C_1-C_6)$alkylamino groups;

(xii) a group of the formula:

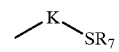

where

K is as defined above for ix, and $R_7$ is hydrogen, lower alkyl having 1–6 carbon atoms, or cycloalkyl having 3–7 carbon atoms;

(xiii) a group of the formula:

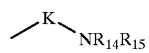

where

K is as defined above for ix; and $R_{14}$ and $R_{15}$ independently represent hydrogen, lower alkyl having 1–6 carbon atoms, cycloalkyl having 3–7 carbon atoms, or —$SO_2R_8$ where $R_8$ is as defined above, or $R_{14}$ and $R_{15}$ together with the nitrogen atom to which they are attached form a heterocyclic moiety;

(xiv) a group of the formula:

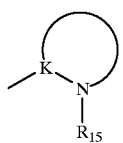

where K and $R_{15}$ are as defined above in ix and xii, respectively;

(xv) a group of the formula:

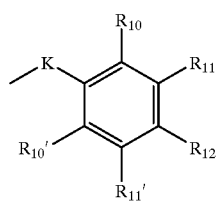

where
K is as defined above for ix;
$R_{10}$ and $R_{10}'$ are the same or different and are selected from hydrogen, halogen, hydroxy, lower alkoxy having 1–6 carbon atoms, and cycloalkoxy having 3–7 carbon atoms;
$R_{11}$, $R_{11}'$, and $R_{12}$ are the same or different and are selected from hydrogen, halogen, hydroxy, —$OR_4$, —$CR_7(R_9)NR_5R_6$, —$CR_7(R_{16})OR_4$, or $R_{11}$–$R_{12}$ taken together with the atoms to which they are attached form a (hetero)cyclic ring; and
$R_{16}$ is hydrogen, lower alkyl having 1–6 carbon atoms, or cycloalkyl having 3–7 carbon atoms;

(xvi) a group of the formula:

where K is as defined above for ix; and W is heteroaryl;

(xvii) a group of the formula:

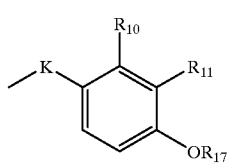

where
K is as defined above for ix; $R_{10}$ and $R_{11}$ are as defined above for xv, and
$R_{17}$ is hydrogen, lower alkyl, or ($C_3$–$C_7$)cycloalkyl, where the alkyl or cycloalkyl is optionally substituted with halogen, lower alkoxy, or mono- or di($C_1$–$C_6$)alkylamino;

(xviii) a group of the formula:

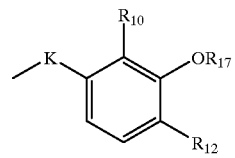

where K, $R_{10}$, $R_{12}$, and $R_{17}$ are as defined above;

(xix) a group of the formula:

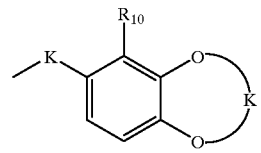

where each K is independently defined as above for ix and $R_{10}$ is defined above;

(xx) a group of the formula:

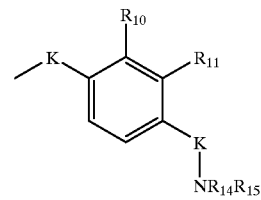

where K, $R_{10}$, $R_{11}$, $R_{14}$, and $R_{15}$ are as defined above; or (xxi) a group of the formula:

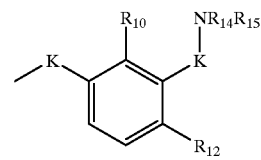

where K, $R_{10}$, $R_{12}$, $R_{14}$, and $R_{15}$ are as defined above.

3. A pharmaceutical composition according to claim 1, comprising a compound of Formula B, or a pharmaceutically acceptable salt thereof, and a pharmaceutically acceptable carrier:

Formula B

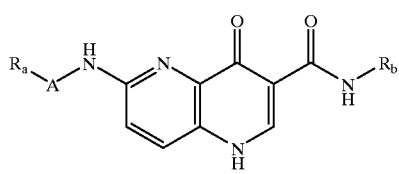

wherein
A is $C_1$–$C_6$ alkylene;
$R_a$ is phenyl optionally mono-, di-, or trisubstituted with halogen, lower alkyl, lower alkoxy, or mono- or di-$C_1$–$C_6$ alkylamino, or mono- or di-$C_1$–$C_6$ alkylamino lower alkyl; and $R_b$ is lower alkyl or lower cycloalkyl.

4. A pharmaceutical composition according to claim 1, comprising a compound of Formula C, or a pharmaceutically acceptable salt thereof, and a pharmaceutically acceptable carrier,

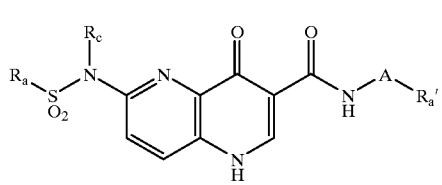

Formula C wherein

A is $C_1$–$C_6$ alkylene;

$R_a$ and $R_a'$ are independently phenyl groups optionally mono-, di-, or trisubstituted with halogen, lower alkyl, lower alkoxy, or mono- or di-$C_1$–$C_6$ alkylamino, or mono- or di-$C_1$–$C_6$ alkylamino lower alkyl; and $R_c$ is hydrogen or lower alkyl.

5. A pharmaceutical composition according to claim 1, comprising a compound of Formula D, or a pharmaceutically acceptable salt thereof, and a pharmaceutically acceptable carrier,

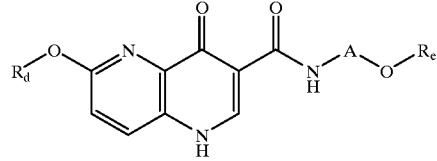

Formula D wherein

A is $C_1$–$C_6$ alkylene; and $R_d$ and $R_e$ are independently lower alkyl groups.

6. A pharmaceutical composition according to claim 1, comprising a compound of Formula E, or a pharmaceutically acceptable salt thereof, and a pharmaceutically acceptable carrier,

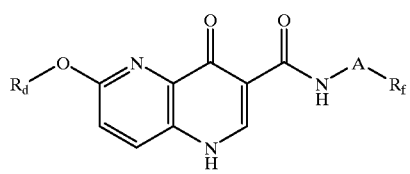

Formula E wherein

A is $C_1$–$C_6$ alkylene;

$R_d$ is lower alkyl;

$R_f$ is a group of the formula:

where

E is oxygen or nitrogen; and

M is $C_1$–$C_3$ alkylene or nitrogen.

7. A pharmaceutical composition according to claim 1, comprising a compound of Formula F, or a pharmaceutically acceptable salt thereof, and a pharmaceutically acceptable carrier,

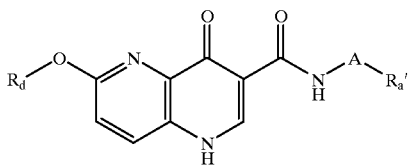

Formula F wherein

A is $C_1$–$C_6$ alkylene;

$R_d$ is lower alkyl; and $R_a'$ is phenyl optionally mono-, di-, or trisubstituted with halogen, lower alkyl, lower alkoxy, or mono- or di-$C_1$–$C_6$ alkylamino, or mono- or di-$C_1$–$C_6$ alkylamino lower alkyl.

8. A pharmaceutical composition according to claim 1, comprising a compound of Formula G, or a pharmaceutically acceptable salt thereof, and a pharmaceutically acceptable carrier,

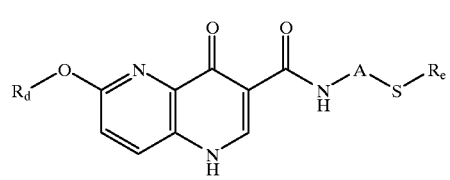

Formula G wherein

A is $C_1$–$C_6$ alkylene; and $R_d$ and $R_e$ are independently lower alkyl groups.

9. A pharmaceutical composition according to claim 1, comprising a compound of Formula H, or a pharmaceutically acceptable salt thereof, and a pharmaceutically acceptable carrier,

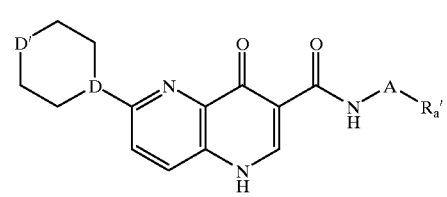

Formula H wherein

D is nitrogen or CH;

D' is nitrogen or oxygen;

A is $C_1$–$C_6$ alkylene; and $R_a'$ is phenyl optionally mono-, di-, or trisubstituted with halogen, lower alkyl, lower alkoxy, or mono- or di-$C_1$–$C_6$ alkylamino, or mono- or di-$C_1$–$C_6$ alkylamino lower alkyl.

10. A pharmaceutical composition according to claim 1, comprising a compound of Formula I, or a pharmaceutically acceptable salt thereof, and a pharmaceutically acceptable carrier,

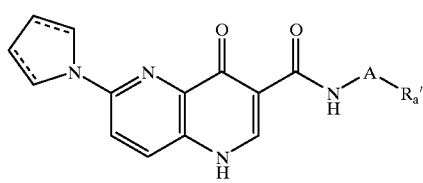

Formula I

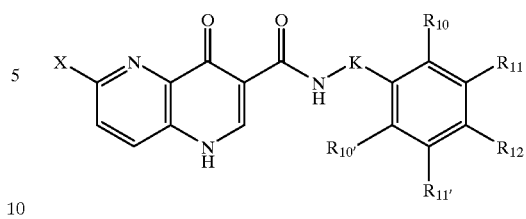

Formula L wherein

A is $C_1$–$C_6$ alkylene; and $R_a'$ is phenyl optionally mono-, di-, or trisubstituted with halogen, lower alkyl, lower alkoxy, or mono- or di-$C_1$–$C_6$ alkylamino, or mono- or di-$C_1$–$C_6$ alkylamino lower alkyl.

11. A pharmaceutical composition according to claim 1, comprising a compound of Formula J, or a pharmaceutically acceptable salt thereof, and a pharmaceutically acceptable carrier,

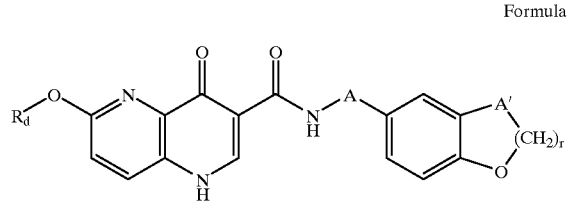

Formula J wherein

A is $C_1$–$C_6$ alkylene; and $R_d$ is lower alkyl;

A' represents oxygen or methylene; and r is an integer of from 1–3.

12. A pharmaceutical composition according to claim 1, comprising a compound of Formula K, or a pharmaceutically acceptable salt thereof, and a pharmaceutically acceptable carrier,

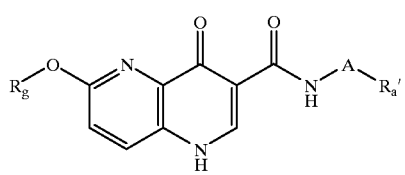

Formula K wherein

A is $C_1$–$C_6$ alkylene;

$R_g$ is lower alkyloxy lower alkyl; and $R_a'$ is phenyl optionally mono-, di-, or trisubstituted with halogen, lower alkyl, lower alkoxy, or mono- or di-$C_1$–$C_6$ alkylamino, or mono- or di-$C_1$–$C_6$ alkylamino lower alkyl.

13. A pharmaceutical composition comprising a compound of Formula L, or a pharmaceutically acceptable salt thereof, and a pharmaceutically acceptable carrier, wherein:

X is hydrogen, halogen, mono- or di($C_1$–$C_6$)alkylamino, or ($C_1$–$C_6$) alkoxy;

$R_{10}$ and $R_{10'}$ are the same or different and may be selected from hydrogen, ($C_1$–$C_6$)alkyl, halogen, hydroxy, ($C_1$–$C_6$)alkoxy, or ($C_3$–$C_7$) cycloalkoxy;

$R_{11}$, $R_{11'}$, and $R_{12}$ are the same or different and may be selected from hydrogen, ($C_1$–$C_6$)alkyl, halogen, hydroxy, —$OR_4$, —$CR_7(R_9)NR_5R_6$, or —$CR_7(R_9)OR_4$;

$R_4$ is hydrogen, ($C_1$–$C_6$)alkyl, or ($C_3$–$C_7$), and may be optionally substituted with one or more ($C_1$–$C_6$)alkoxy or mono- or di($C_1$–$C_6$) alkylamino groups;

$R_5$ and $R_6$ independently represent hydrogen, lower alkyl having 1–6 carbon atoms, ($C_3$–$C_7$)cycloalkyl, —$SO_2R_8$ where $R_8$ is ($C_1$–$C_6$)alkyl, ($C_3$–$C_7$)cycloalkyl, or optionally substituted phenyl, $R_7$ is hydrogen, ($C_1$–$C_6$)alkyl, or ($C_3$–$C_7$)cycloalkyl; and $R_9$ is hydrogen, lower alkyl, or ($C_3$–$C_7$)cycloalkyl, where the alkyl or cycloalkyl is optionally substituted with halogen, lower alkoxy, or mono- or di($C_1$–$C_6$) alkylamino.

14. A pharmaceutical composition according to claim 13 wherein:

$R_{11}$, $R_{11'}$, and $R_{12}$ are the same or different and are independently selected from hydrogen, ($C_1$–$C_6$)alkyl, halogen, and hydroxy.

15. A pharmaceutical composition according to claim 1, wherein the compound is N-n-Butyl 6-benzylamino-4-oxo-1,4-dihydro-1,5-naphthyridine-3-carboxamide or a pharmaceutically acceptable salt thereof.

16. A pharmaceutical composition according to claim 1, wherein the compound is N-[2-(Ethylthio)ethyl] 6-methoxy-4-oxo-1,4-dihydro-1,5-napththyridine-3-carboxamide or a pharmaceutically acceptable salt thereof.

17. A pharmaceutical composition according to claim 1, wherein the compound is N-[4-(Methylaminomethyl)benzyl] 6-(2-methoxyethoxy)-4-oxo-1,4-dihydro-1,5-naphthyridine-3-carboxamide or a pharmaceutically acceptable salt thereof.

18. A pharmaceutical composition according to claim 1, wherein the compound is N-(4-Methoxybenzyl) 6-pyrrolidino-4-oxo-1,4-dihydro-1,5-naphthyridine-3-carboxamide or a pharmaceutically acceptable salt thereof.

19. A pharmaceutical composition according to claim 1, wherein the compound is N-n-Butyl 6-chloro-4-oxo-1,4-tetrahydro-1,5-naphthyridine-3-carboxamide or a pharmaceutically acceptable salt thereof.

20. A pharmaceutical composition according to claim 1, wherein the compound is N-Propan-3-ol 6-methoxy-4-oxo-1,4-tetrahydro-1,5-naphthyridine-3-carboxamide or a pharmaceutically acceptable salt thereof.

21. A pharmaceutical composition according to claim 1, wherein the compound is N-n-Butyl 6-ethoxy-4-oxo-1,4-tetrahydro-1,5-naphthyridine-3-carboxamide or a pharmaceutically acceptable salt thereof.

22. A pharmaceutical composition according to claim 1, wherein the compound is N-(2-Ethylthio)ethyl 6-methoxy-4-oxo-1,4-tetrahydro-1,5-naphthyridine-3-carboxamide or a pharmaceutically acceptable salt thereof.

23. A pharmaceutical composition according to claim 1, wherein the compound is N-n-Butyl 6-(N-benzylamino)-4-oxo-1,4-tetrahydro-1,5-naphthyridine-3-carboxamide or a pharmaceutically acceptable salt thereof.

24. A pharmaceutical composition according to claim 1, wherein the compound is N-n-Pentyl 6-ethoxy-4-oxo-1,4-tetrahydro-1,5-naphthyridine-3-carboxamide or a pharmaceutically acceptable salt thereof.

25. A pharmaceutical composition according to claim 1, wherein the compound is N-(3-Isopropoxy)propyl 6-ethoxy-4-oxo-1,4-tetrahydro-1,5-naphthyridine-3-carboxamide or a pharmaceutically acceptable salt thereof.

26. A pharmaceutical composition according to claim 1, wherein the compound is N-Benzyl 6-ethoxy-4-oxo-1,4-tetrahydro-1,5-naphthyridine-3-carboxamide or a pharmaceutically acceptable salt thereof.

27. A pharmaceutical composition according to claim 1, wherein the compound is N-2-Pentyl 6-ethoxy-4-oxo-1,4-tetrahydro-1,5-naphthyridine-3-carboxamide or a pharmaceutically acceptable salt thereof.

28. A pharmaceutical composition according to claim 1, wherein the compound is N-(2-Tetrahydrofuranyl)methyl 6-ethoxy-4-oxo-1,4-tetrahydro-1,5-naphthyridine-3-carboxamide or a pharmaceutically acceptable salt thereof.

29. A pharmaceutical composition according to claim 1, wherein the compound is N-(3-Methoxy)propan-2-ol 6-ethoxy-4-oxo-1,4-tetrahydro-1,5-naphthyridine-3-carboxamide or a pharmaceutically acceptable salt thereof.

30. A pharmaceutical composition according to claim 1, wherein the compound is N-(3-Methoxy)propyl 6-ethoxy-4-oxo-1,4-tetrahydro-1,5-naphthyridine-3-carboxamide or a pharmaceutically acceptable salt thereof.

31. A pharmaceutical composition according to claim 1, wherein the compound is N-(2-Methoxy)ethyl 6-ethoxy-4-oxo-1,4-tetrahydro-1,5-naphthyridine-3-carboxamide or a pharmaceutically acceptable salt thereof.

32. A pharmaceutical composition according to claim 1, wherein the compound is N-Isoamyl 6-ethoxy-4-oxo-1,4-tetrahydro-1,5-naphthyridine-3-carboxamide or a pharmaceutically acceptable salt thereof.

33. A pharmaceutical composition according to claim 1, wherein the compound is N-(2-Furanyl)methyl 6-ethoxy-4-oxo-1,4-tetrahydro-1,5-naphthyridine-3-carboxamide or a pharmaceutically acceptable salt thereof.

34. A pharmaceutical composition according to claim 1, wherein the compound is N-(3-Methoxybenzyl) 6-ethoxy-4-oxo-1,4-tetrahydro-1,5-naphthyridine-3-carboxamide or a pharmaceutically acceptable salt thereof.

35. A pharmaceutical composition according to claim 1, wherein the compound is N-(3-Ethoxy)propyl 6-ethoxy-4-oxo-1,4-tetrahydro-1,5-naphthyridine-3-carboxamide or a pharmaceutically acceptable salt thereof.

36. A pharmaceutical composition according to claim 1, wherein the compound is N-2-(2-Methyl)butyl 6-ethoxy-4-oxo-1,4-tetrahydro-1,5-naphthyridine-3-carboxamide or a pharmaceutically acceptable salt thereof.

37. A pharmaceutical composition according to claim 1, wherein the compound is N-2-Pentan-1-ol 6-ethoxy-4-oxo-1,4-tetrahydro-1,5-naphthyridine-3-carboxamide or a pharmaceutically acceptable salt thereof.

38. A pharmaceutical composition according to claim 1, wherein the compound is N-5-Pentanol 6-ethoxy-4-oxo-1,4-tetrahydro-1,5-naphthyridine-3-carboxamide or a pharmaceutically acceptable salt thereof.

39. A pharmaceutical composition according to claim 1, wherein the compound is N-1-Cyclohexan-2-ol 6-ethoxy-4-oxo-1,4-tetrahydro-1,5-naphthyridine-3-carboxamide or a pharmaceutically acceptable salt thereof.

40. A pharmaceutical composition according to claim 1, wherein the compound is N-Benzyl 6-methoxy-4-oxo-1,4-tetrahydro-1,5-naphthyridine-3-carboxamide or a pharmaceutically acceptable salt thereof.

41. A pharmaceutical composition according to claim 1, wherein the compound is N-(2-Fluorobenzyl) 6-methoxy-4-oxo-1,4-tetrahydro-1,5-naphthyridine-3-carboxamide or a pharmaceutically acceptable salt thereof.

42. A pharmaceutical composition according to claim 1, wherein the compound is N-(3-Fluorobenzyl) 6-methoxy-4-oxo-1,4-tetrahydro-1,5-naphthyridine-3-carboxamide or a pharmaceutically acceptable salt thereof.

43. A pharmaceutical composition according to claim 1, wherein the compound is N-(4-Fluorobenzyl) 6-methoxy-4-oxo-1,4-tetrahydro-1,5-naphthyridine-3-carboxamide or a pharmaceutically acceptable salt thereof.

44. A pharmaceutical composition according to claim 1, wherein the compound is N-(4/5-Imidazolyl)methyl 6-ethoxy-4-oxo-1,4-tetrahydro-1,5-naphthyridine-3-carboxamide or a pharmaceutically acceptable salt thereof.

45. A pharmaceutical composition according to claim 1, wherein the compound is N-4-Tetrahydropyranyl 6-ethoxy-4-oxo-1,4-tetrahydro-1,5-naphthyridine-3-carboxamide or a pharmaceutically acceptable salt thereof.

46. A pharmaceutical composition according to claim 1, wherein the compound is N-(3-Thienyl)methyl 6-ethoxy-4-oxo-1,4-tetrahydro-1,5-naphthyridine-3-carboxamide or a pharmaceutically acceptable salt thereof.

47. A pharmaceutical composition according to claim 1, wherein the compound is N-2-(6-Methyl)heptan-6-ol 6-ethoxy-4-oxo-1,4-tetrahydro-1,5-naphthyridine-3-carboxamide or a pharmaceutically acceptable salt thereof.

48. A pharmaceutical composition according to claim 1, wherein the compound is N-(2-Tetrahydropyranyl)methyl 6-ethoxy-4-oxo-1,4-tetrahydro-1,5-naphthyridine-3-carboxamide or a pharmaceutically acceptable salt thereof.

49. A pharmaceutical composition according to claim 1, wherein the compound is N-(2-Fluorobenzyl) 6-ethoxy-4-oxo-1,4-tetrahydro-1,5-naphthyridine-3-carboxamide or a pharmaceutically acceptable salt thereof.

50. A pharmaceutical composition according to claim 1, wherein the compound is N-(3-Fluorobenzyl) 6-ethoxy-4-oxo-1,4-tetrahydro-1,5-naphthyridine-3-carboxamide or a pharmaceutically acceptable salt thereof.

51. A pharmaceutical composition according to claim 1, wherein the compound is N-(4-Fluorobenzyl) 6-ethoxy-4-oxo-1,4-tetrahydro-1,5-naphthyridine-3-carboxamide or a pharmaceutically acceptable salt thereof.

52. A pharmaceutical composition according to claim 1, wherein the compound is N-(4-Methoxybenzyl) 6-ethoxy-4-oxo-1,4-tetrahydro-1,5-naphthyridine-3-carboxamide or a pharmaceutically acceptable salt thereof.

53. A pharmaceutical composition according to claim 1, wherein the compound is N-(3-Fluorobenzyl) 6-methoxy-4-oxo-1,4-tetrahydro-1,5-naphthyridine-3-carboxamide or a pharmaceutically acceptable salt thereof.

54. A pharmaceutical composition according to claim 1, wherein the compound is N-Benzyl 6-(N-methyl,N-toluenesulfonyl-amino)-4-oxo-1,4-tetrahydro-1,5-naphthyridine-3-carboxamide or a pharmaceutically acceptable salt thereof.

55. A pharmaceutical composition according to claim 1, wherein the compound is N-Benzyl 6-(methylamino)-4-oxo- 1,4-tetrahydro-1,5-naphthyridine-3-carboxamide or a pharmaceutically acceptable salt thereof.

56. A pharmaceutical composition according to claim 1, wherein the compound is N-Piperonyl 6-ethoxy-4-oxo-1,4-tetrahydro-1,5-naphthyridine-3-carboxamide or a pharmaceutically acceptable salt thereof.

57. A pharmaceutical composition according to claim 1, wherein the compound is N-Piperonyl 6-methoxy-4-oxo-1,4-tetrahydro-1,5-naphthyridine-3-carboxamide or a pharmaceutically acceptable salt thereof.

58. A pharmaceutical composition according to claim 1, wherein the compound is N-2-(4/5-Imidazolyl)ethyl 6-ethoxy-4-oxo-1,4-tetrahydro-1,5-naphthyridine-3-carboxamide or a pharmaceutically acceptable salt thereof.

59. A pharmaceutical composition according to claim 1, wherein the compound is N-(4-Methylbenzyl) 6-ethoxy-4-oxo-1,4-tetrahydro-1,5-naphthyridine-3-carboxamide or a pharmaceutically acceptable salt thereof.

60. A pharmaceutical composition according to claim 1, wherein the compound is N-Benzyl 6-(2-methoxyethoxy)-4-oxo-1,4-tetrahydro-1,5-naphthyridine-3-carboxamide or a pharmaceutically acceptable salt thereof.

61. A pharmaceutical composition according to claim 1, wherein the compound is N-Benzyl 6-dimethylamino-4-oxo-1,4-tetrahydro-1,5-naphthyridine-3-carboxamide or a pharmaceutically acceptable salt thereof.

62. A pharmaceutical composition according to claim 1, wherein the compound is N-Isoamyl 6-morpholino-4-oxo-1,4-tetrahydro-1,5-naphthyridine-3-carboxamide or a pharmaceutically acceptable salt thereof.

63. A pharmaceutical composition according to claim 1, wherein the compound is N-Benzyl 6-morpholino-4-oxo-1,4-tetrahydro-1,5-naphthyridine-3-carboxamide or a pharmaceutically acceptable salt thereof.

64. A pharmaceutical composition according to claim 1, wherein the compound is N-(2-Fluorobenzyl) 6-morpholino-4-oxo-1,4-tetrahydro-1,5-naphthyridine-3-carboxamide or a pharmaceutically acceptable salt thereof.

65. A pharmaceutical composition according to claim 1, wherein the compound is N-(3-Ethoxy)propyl 6-morpholino-4-oxo-1,4-tetrahydro-1,5-naphthyridine-3-carboxamide or a pharmaceutically acceptable salt thereof.

66. A pharmaceutical composition according to claim 1, wherein the compound is N-n-Butyl 6-morpholino-4-oxo-1,4-tetrahydro-1,5-naphthyridine-3-carboxamide or a pharmaceutically acceptable salt thereof.

67. A pharmaceutical composition according to claim 1, wherein the compound is N-(2-Pyridyl)methyl 6-morpholino-4-oxo-1,4-tetrahydro-1,5-naphthyridine-3-carboxamide or a pharmaceutically acceptable salt thereof.

68. A pharmaceutical composition according to claim 1, wherein the compound is N-(2-Thienyl)methyl 6-(2-methoxyethoxy)-4-oxo-1,4-tetrahydro-1,5-naphthyridine-3-carboxamide or a pharmaceutically acceptable salt thereof.

69. A pharmaceutical composition according to claim 1, wherein the compound is N-Isoamyl 6-dimethylamino-4-oxo-1,4-tetrahydro-1,5-naphthyridine-3-carboxamide or a pharmaceutically acceptable salt thereof.

70. A pharmaceutical composition according to claim 1, wherein the compound is N-(2-Thienyl)methyl 6-morpholino-4-oxo-1,4-tetrahydro-1,5-naphthyridine-3-carboxamide or a pharmaceutically acceptable salt thereof.

71. A pharmaceutical composition according to claim 1, wherein the compound is N-(2-Thienyl)methyl 6-dimethylamino-4-oxo-1,4-tetrahydro-1,5-naphthyridine-3-carboxamide or a pharmaceutically acceptable salt thereof.

72. A pharmaceutical composition according to claim 1, wherein the compound is N-(2-Thiazolyl)methyl 6-morpholino-4-oxo-1,4-tetrahydro-1,5-naphthyridine-3-carboxamide or a pharmaceutically acceptable salt thereof.

73. A pharmaceutical composition according to claim 1, wherein the compound is N-(4-Methylaminomethyl)benzyl 6-ethoxy-4-oxo-1,4-tetrahydro-1,5-naphthyridine-3-carboxamide or a pharmaceutically acceptable salt thereof.

74. A pharmaceutical composition according to claim 1, wherein the compound is N-[4-(1-Methylamino)ethyl]benzyl 6-ethoxy-4-oxo-1,4-tetrahydro-1,5-naphthyridine-3-carboxamide or a pharmaceutically acceptable salt thereof.

75. A pharmaceutical composition according to claim 1, wherein the compound is N-(2-Tetrahydrofuranyl)methyl 6-dimethylamino-4-oxo-1,4-tetrahydro-1,5-naphthyridine-3-carboxamide or a pharmaceutically acceptable salt thereof.

76. A pharmaceutical composition according to claim 1, wherein the compound is N-n-Pentyl 6-morpholino-4-oxo-1,4-tetrahydro-1,5-naphthyridine-3-carboxamide or a pharmaceutically acceptable salt thereof.

77. A pharmaceutical composition according to claim 1, wherein the compound is N-(3-Methoxybenzyl) 6-morpholino-4-oxo-1,4-tetrahydro-1,5-naphthyridine-3-carboxamide or a pharmaceutically acceptable salt thereof.

78. A pharmaceutical composition according to claim 1, wherein the compound is N-(3-Fluorobenzyl) 6-morpholino-4-oxo-1,4-tetrahydro-1,5-naphthyridine-3-carboxamide or a pharmaceutically acceptable salt thereof.

79. A pharmaceutical composition according to claim 1, wherein the compound is N-(4-Methylaminomethyl)benzyl 6-(2-methoxyethoxy)-4-oxo-1,4-tetrahydro-1,5-naphthyridine-3-carboxamide or a pharmaceutically acceptable salt thereof.

80. A pharmaceutical composition according to claim 1, wherein the compound is N-n-Butyl 6-pyrrolidino-4-oxo-1,4-tetrahydro-1,5-naphthyridine-3-carboxamide or a pharmaceutically acceptable salt thereof.

81. A pharmaceutical composition according to claim 1, wherein the compound is N-(4-Methoxybenzyl) 6-pyrrolidino-4-oxo-1,4-tetrahydro-1,5-naphthyridine-3-carboxamide or a pharmaceutically acceptable salt thereof.

82. A pharmaceutical composition according to claim 1, wherein the compound is N-(2-Thienyl)methyl 6-pyrrolidino-4-oxo-1,4-tetrahydro-1,5-naphthyridine-3-carboxamide or a pharmaceutically acceptable salt thereof.

83. A pharmaceutical composition according to claim 1, wherein the compound is N-(4-Methylamino)benzyl 6-n-propoxy-4-oxo-1,4-tetrahydro-1,5-naphthyridine-3-carboxamide hydrochloride, or a pharmaceutically acceptable salt thereof.

84. A pharmaceutical composition according to claim 1, wherein the compound is N-[4-(1-Methylaminomethyl)ethyl]benzyl 6-chloro-4-oxo-1,4-tetrahydro-1,5-naphthyridine-3-carboxamide or a pharmaceutically acceptable salt thereof.

85. A pharmaceutical composition according to claim 1, wherein the compound is N-[4-(1-Methylamino)ethyl]benzyl 6-pyrrolidino-4-oxo-1,4-tetrahydro-1,5-naphthyridine-3-carboxamide hydrochloride, or a pharmaceutically acceptable salt thereof.

86. A pharmaceutical composition according to claim 1, wherein the compound is N-(4-Ethoxybenzyl) 6-morpholino-4-oxo-1,4-tetrahydro-1,5-naphthyridine-3-carboxamide or a pharmaceutically acceptable salt thereof.

87. A pharmaceutical composition according to claim 1, wherein the compound is N-(4-Ethoxybenzyl)

6-pyrrolidino-4-oxo-1,4-tetrahydro-1,5-naphthyridine-3-carboxamide or a pharmaceutically acceptable salt thereof.

88. A pharmaceutical composition according to claim 1, wherein the compound is N-(4-Chlorobenzyl) 6-morpholino-4-oxo-1,4-tetrahydro-1,5-naphthyridine-3-carboxamide or a pharmaceutically acceptable salt thereof.

89. A pharmaceutical composition according to claim 1, wherein the compound is N-(3-Chlorobenzyl) 6-morpholino-4-oxo-1,4-tetrahydro-1,5-naphthyridine-3-carboxamide or a pharmaceutically acceptable salt thereof.

90. A pharmaceutical composition according to claim 1, wherein the compound is N-Piperonyl 6-dimethylamino-4-oxo-1,4-tetrahydro-1,5-naphthyridine-3-carboxamide hydrochloride, or a pharmaceutically acceptable salt thereof.

91. A pharmaceutical composition according to claim 1, wherein the compound is N-Benzyl 6-(2-methylamino) ethoxy-4-oxo-1,4-tetrahydro-1,5-naphthyridine-3-carboxamide or a pharmaceutically acceptable salt thereof.

92. A pharmaceutical composition according to claim 1, wherein the compound is N-Benzyl 6-(2-dimethylamino) ethoxy-4-oxo-1,4-tetrahydro-1,5-naphthyridine-3-carboxamide or a pharmaceutically acceptable salt thereof.

93. A pharmaceutical composition according to claim 1, wherein the compound is N-(4-Ethylaminomethyl)benzyl 6-ethoxy-4-oxo-1,4-tetrahydro-1,5-naphthyridine-3-carboxamide or a pharmaceutically acceptable salt thereof.

94. A pharmaceutical composition according to claim 1, wherein the compound is N-Benzyl 6-(2-methoxy) ethylamino-4-oxo-1,4-tetrahydro-1,5-naphthyridine-3-carboxamide or a pharmaceutically acceptable salt thereof.

95. A pharmaceutical composition according to claim 1, wherein the compound is N-(3-Methylaminomethyl)benzyl 6-ethoxy-4-oxo-1,4-tetrahydro-1,5-naphthyridine-3-carboxamide hydrochloride, or a pharmaceutically acceptable salt thereof.

96. A pharmaceutical composition according to claim 1, wherein the compound is N-(4-Dimethylaminomethyl) benzyl 6-ethoxy-4-oxo-1,4-tetrahydro-1,5-naphthyridine-3-carboxamide hydrochloride, or a pharmaceutically acceptable salt thereof.

97. A pharmaceutical composition according to claim 1, wherein the compound is N-(3-Methylaminomethyl)benzyl 6-n-propoxy-4-oxo-1,4-tetrahydro-1,5-naphthyridine-3-carboxamide hydrochloride, or a pharmaceutically accept-able salt thereof.

98. A pharmaceutical composition according to claim 1, wherein the compound is N-[4-(1-Imidazolylmethy)]benzyl 6-ethoxy-4-oxo-1,4-tetrahydro-1,5-naphthyridine-3-carboxamide or a pharmaceutically acceptable salt thereof.

99. A pharmaceutical composition according to claim 1, wherein Y is pyrimidinylmethyl, pyridylmethyl, or a group of the formula:

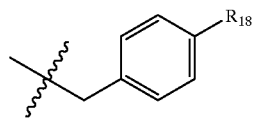

where $R_{18}$ represents hydrogen, amino, mono-, or di($C_1$–$C_6$)alkylamino, or $C_1$–$C_6$ alkyl.

100. A pharmaceutical composition according to claim 1, comprising a compound of Formula M, or a pharmaceutically acceptable salt thereof, and a pharmaceutically acceptable carrier

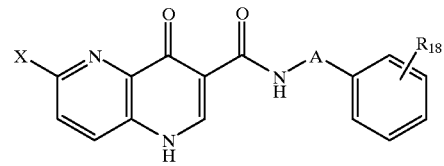

Formula M wherein

A is $C_1$–$C_6$ alkylene;

X is defined as above for Formula I in claim 1; and $R_{18}$ is amino or mono- or di($C_1$–$C_6$)alkylamino; or lower alkyl optionally substituted with

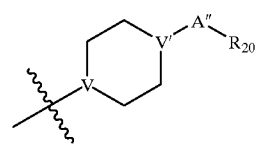

where

V and V' are independently CH or nitrogen;

A" is $C_1$–$C_6$ alkylene; and $R_{20}$ is phenyl, pyridyl, or pyrimidinyl, each of which is optionally mono-, di-, or trisubstituted independently with halogen, hydroxy, $C_1$–$C_6$ alkoxy, amino, or mono- or di($C_1$–$C_6$)alkylamino.

101. A pharmaceutical composition according to claim 1, wherein the compound is N-Benzyl 6-benzylamino-4-oxo-1,4-tetrahydro-1,5-naphthyridine-3-carboxamide or a pharmaceutically acceptable salt thereof.

102. A pharmaceutical composition according to claim 1, wherein the compound is N-Cyclohexyl 6-ethoxy-4-oxo-1,4-tetrahydro-1,5-naphthyridine-3-carboxamide or a pharmaceutically acceptable salt thereof.

103. A pharmaceutical composition according to claim 1, wherein the compound is N-Cyclohexylmethyl 6-ethoxy-4-oxo-1,4-tetrahydro-1,5-naphthyridine-3-carboxamide or a pharmaceutically acceptable salt thereof.

104. A pharmaceutical composition according to claim 1, wherein the compound is N-(4-Aminobenzyl)-6-ethoxy-4-oxo-1,4-tetrahydro-1,5-naphthyridine-3-carboxamide or a pharmaceutically acceptable salt thereof.

105. A pharmaceutical composition according to claim 1, wherein the compound is N-(4-Pyridylmethyl) 6-ethoxy-4-oxo-1,4-tetrahydro-1,5-naphthyridine-3-carboxamide or a pharmaceutically acceptable salt thereof.

106. A pharmaceutical composition according to claim 1, wherein the compound is N-Benzyl 6-tetrahydroisoquinolinyl-4-oxo-1,4-tetrahydro-1,5-naphthyridine-3-carboxamide or a pharmaceutically acceptable salt thereof.

107. A pharmaceutical composition according to claim 1, wherein the compound is N-{4-[1-[4-(4-Fluorobenzyl) piperazinyl]methyl]benzyl}6-(2,2,2-trifluoroethyl)-4-oxo-1,4-tetrahydro-1,5-naphthyridine-3-carboxamide or a pharmaceutically acceptable salt thereof.

* * * * *